US011865162B2

(12) United States Patent
Xie et al.

(10) Patent No.: US 11,865,162 B2
(45) Date of Patent: Jan. 9, 2024

(54) COMPOSITIONS AND METHODS FOR TREATMENT OF UREMIC CARDIOMYOPATHY

(71) Applicant: MARSHALL UNIVERSITY RESEARCH CORPORATION, Huntington, WV (US)

(72) Inventors: Zijian Xie, Huntington, WV (US); Joseph I. Shapiro, Huntington, WV (US); Jiang Liu, Huntington, WV (US)

(73) Assignee: MARSHALL UNIVERSITY RESEARCH CORPORATION, Huntington, WV (US)

( * ) Notice: Subject to any disclaimer, the term of this patent is extended or adjusted under 35 U.S.C. 154(b) by 244 days.

(21) Appl. No.: 16/313,741

(22) PCT Filed: Jun. 30, 2017

(86) PCT No.: PCT/US2017/040329
§ 371 (c)(1),
(2) Date: Dec. 27, 2018

(87) PCT Pub. No.: WO2018/005990
PCT Pub. Date: Jan. 4, 2018

(65) Prior Publication Data
US 2020/0085918 A1    Mar. 19, 2020

Related U.S. Application Data
(60) Provisional application No. 62/357,535, filed on Jul. 1, 2016.

(51) Int. Cl.
*A61K 38/46* (2006.01)
*A61K 38/00* (2006.01)
*A61P 9/10* (2006.01)

(52) U.S. Cl.
CPC ............ *A61K 38/46* (2013.01); *A61K 38/005* (2013.01); *A61P 9/10* (2018.01)

(58) Field of Classification Search
CPC ......... A61K 38/005; A61K 38/46; A61P 9/10; C12Y 306/03009
See application file for complete search history.

(56) References Cited

U.S. PATENT DOCUMENTS

| 2011/0021433 | A1  | 1/2011  | Harlan et al. | |
|---|---|---|---|---|
| 2011/0245167 | A1* | 10/2011 | Xie ....................... | A61K 38/46 514/7.5 |
| 2013/0065267 | A1  | 3/2013  | Mao | |
| 2014/0113969 | A1  | 4/2014  | Cooper et al. | |
| 2015/0133389 | A1* | 5/2015  | Xie .................... | C07K 14/4705 514/19.5 |
| 2016/0106800 | A1  | 4/2016  | Szeto et al. | |
| 2019/0298720 | A1* | 10/2019 | Nandabalan ......... | C07D 487/00 |

FOREIGN PATENT DOCUMENTS

| EP | 0813877 A2 | 12/1997 | |
|---|---|---|---|
| WO | WO-2017214514 A1 * | 12/2017 | ........... C07D 487/00 |

OTHER PUBLICATIONS

Ravish Shah, Anemia associated with chronic heart failure: current concepts, Clinical Interventions in Aging 2013:8 111-122.*
Eyad Alhaj, Uremic Cardiomyopathy: An Underdiagnosed Disease, Congest Heart Fail. 2013;19:E40-E45.*
Fangfang Lai, Identification of a Mutant α1 Na/K-ATPase That Pumps but Is Defective in Signal Transduction, The Journal of Biological Chemistry vol. 288, No. 19, pp. 13295-13304, May 10, 2013.*
Cirino, https://www.healthline.com/health/cancer/anemia-cancer#anemia-and-cancer-link, accessed on Mar. 25, 2021.*
KDIGO (Clinical Practice Guideline for Anemia in Chronic Kidney Disease, vol. 2, issue 4, 2012, pp. 1-64).*
J. Liu et al., Ouabain interaction with cardiac Na+/K+-ATPase initiates signal cascades independent of changes in intracellular Na+ and Ca2+ concentrations. J Biol Chem 275, 27838-27844 (2000).
Z. Xie et al., Intracellular reactive oxygen species mediate the linkage of Na+/K+-ATPase to hypertrophy and its marker genes in cardiac myocytes. J Biol Chem 274, 19323-19328 (1999).
M. Liang et al., Identification of a pool of non-pumping Na/K-ATPase. J Biol Chem 282, 10585-10593 (2007).
K. Sodhi et al., pNaKtide inhibits Na/K-ATPase reactive oxygen species amplification and attenuates adipogenesis. Sci Adv 1, e1500781 (2015).
Y. Yan et al., Involvement of reactive oxygen species in a feed-forward mechanism of Na/K-ATPase-mediated signaling transduction. J Biol Chem 288, 34249-34258 (2013).
Z. Li et al., Na/K-ATPase mimetic pNaKtide peptide inhibits the growth of human cancer cells. J Biol Chem 286, 32394-32403 (2011).
Z. Li et al., NaKtide, a Na/K-ATPase-derived peptide Src inhibitor, antagonizes ouabain-activated signal transduction in cultured cells. J Biol Chem 284, 21066-21076 (2009).
J. Lee, S. Kim, Upregulation of heme oxygenase-1 expression by dehydrodiconiferyl alcohol (DHCA) through the AMPK-Nrf2 dependent pathway. Toxicol Appl Pharmacol 281, 87-100 (2014).
Y. Issan et al., Heme oxygenase-1 induction improves cardiac function following myocardial ischemia by reducing oxidative stress. PLOS One 9, e92246 (2014).

(Continued)

Primary Examiner — Julie Ha
Assistant Examiner — Erinne R Dabkowski
(74) Attorney, Agent, or Firm — Stites & Harbison, PLLC; Terry L. Wright

(57) ABSTRACT

Methods for treating uremic cardiomyopathy are provided and include the step of administering a polypeptide antagonist of a Na/K ATPase/Src receptor complex to a subject in need thereof. The polypeptide anatagonist can further include a cell penetrating polypeptide. Methods of treating anemia, including anemia-associated with chronic kidney disease, are also provided.

5 Claims, 26 Drawing Sheets

Specification includes a Sequence Listing.

(56) References Cited

OTHER PUBLICATIONS

A. Asija, S. J. Peterson, D. E. Stec, N. G. Abraham, Targeting endothelial cells with heme oxygenase-1 gene using VE-cadherin promoter attenuates hyperglycemia-mediated cell injury and apoptosis. Antioxid Redox Signal 9, 2065-2074 (2007).
F. T. Botros et al., Induction of heme oxygenase-1 in renovascular hypertension is associated with inhibition of apoptosis. Cell Mol Biol (Noisy-le-grand) 53, 51-60 (2007).
G. M. London, P. S. Parfrey, Cardiac disease in chronic uremia: pathogenesis. Adv Ren Replace Ther 4, 194-211 (1997).
B. Mohmand, D. K. Malhotra, J. I. Shapiro, Uremic cardiomyopathy: role of circulating digitalis like substances. Front Biosci 10, 2036-2044 (2005).
J. Himmelfarb, E. McMonagle, Manifestations of oxidant stress in uremia. Blood Purif 19, 200-205 (2001).
D. M. Okamura, J. Himmelfarb, Tipping the redox balance of oxidative stress in fibrogenic pathways in chronic kidney disease. Pediatr Nephrol 24, 2309-2319 (2009).
J. Himmelfarb, P. Stenvinkel, T. A. Ikizler, R. M. Hakim, The elephant in uremia: oxidant stress as a unifying concept of cardiovascular disease in uremia. Kidney Int 62, 1524-1538 (2002).
B. N. Becker, J. Himmelfarb, W. L. Henrich, R. M. Hakim, Reassessing the cardiac risk profile in chronic hemodialysis patients: a hypothesis on the role of oxidant stress and other non-traditional cardiac risk factors. J Am Soc Nephrol 8, 475-486 (1997).
D. J. Kennedy et al., Partial nephrectomy as a model for uremic cardiomyopathy in the mouse. Am J Physiol Renal Physiol 294, F450-454 (2008).
D. J. Kennedy et al., Central role for the cardiotonic steroid marinobufagenin in the pathogenesis of experimental uremic cardiomyopathy. Hypertension 47, 488-495 (2006).
C. A. Drummond et al., Reduction of Na/K-ATPase affects cardiac remodeling and increases c-kit cell abundance in partial nephrectomized mice. Am J Physiol Heart Circ Physiol 306, H1631-1643 (2014).
S. T. Haller et al., Monoclonal antibody against marinobufagenin reverses cardiac fibrosis in rats with chronic renal failure. Am J Hypertens 25, 690-696 (2012).
J. Tian et al., Spironolactone attenuates experimental uremic cardiomyopathy by antagonizing marinobufagenin. Hypertension 54, 1313-1320 (2009).
R. N. Foley et al., Mode of dialysis therapy and mortality in end-stage renal disease. J Am Soc Nephrol 9, 267-276 (1998).
RStudio-Team, RStudio: Integrated Development for R. RStudio, Inc. Boston, MA. 2015.
R-Core-Team, R: A language and environment for statistical computing. R Foundation for Statistical Computing. Vienna, Austria. 2016.
N. Phillips, yarrr: A companion to the e-book YaRrr!: The Pirate's Guide to R. R package version 0.1. 2016.
J. K. Kruschke, Bayesian estimation supersedes the t test. J Exp Psychol Gen 142, 573-603 (2013).
M. J. Sarnak, et al. Kidney Disease as a Risk Factor for Development of Cardiovascular Disease: A Statement From the American Heart Association Councils on Kidney in Cardiovascular Disease, High Blood Pressure Research, Clinical Cardiology, and Epidemiology and Prevention. Circulation 108, 2154-2169, oi:10.1161/01.cir.0000095676.90936.80 (2003).
A.S. Levey, et al. Controlling the epidemic of cardiovascular disease in chronic renal disease: what do we know? What do we need to learn? Where do we go from here? National Kidney Foundation Task Force on Cardiovascular Disease. Am J Kidney Dis 32, 853-906 (1998).
A. Leelahavanichkul, et al. Angiotensin II overcomes strain-dependent resistance of rapid CKD progression in a new remnant kidney mouse model. Kidney Int 78, 1136-1153, doi:10.1038/ki.2010.287 (2010).
L.J. Ma, et al. A. B. Model of robust induction of glomerulosclerosis in mice: importance of genetic background. Kidney Int 64, 350-355, doi:10.1046/j.1523-1755.2003.00058.x (2003).
Kdoqi & National Kidney, F. KDOQI Clinical Practice Guidelines and Clinical Practice Recommendations for Anemia in Chronic Kidney Disease. Am J Kidney Dis 47, S11-145, doi:10.1053/j.ajkd.2006.03.010 (2006).
J. Arnlov, et al. Myocardial performance index, a Doppler-derived index of global left ventricular function, predicts congestive heart failure in elderly men. European Heart Journal 25, 2220-2225, doi:10.1016/j.ehj.2004.10.021 (2004).
B. G. Brown, et al. Is there any hope for vitamin E? JAMA 293, 1387-1390, doi: 10.1001/jama.293.11.1387 (2005).
E. Alhaj, et al. Uremic Cardiomyopathy: An Underdiagnosed Disease. Congest Heart Fail. 2013;19:E40-E45.
United States Patent and Trademark Office, International Search Report and Written Opinion issued in corresponding Application No. PCT/US17/40329, dated Jan. 2, 2018.
The International Bureau of WIPO, International Preliminary Report on Patentability issued in corresponding Application No. PCT/US17/40329, dated Jan. 10, 2019.

* cited by examiner

D

A

B

A

COMPOSITIONS AND METHODS FOR TREATMENT OF UREMIC CARDIOMYOPATHY

RELATED APPLICATIONS

This application claims priority from U.S. Provisional Application Ser. No. 62/357,535, filed Jul. 1, 2016, the entire disclosure of which is incorporated herein by this reference.

GOVERNMENT INTEREST

This invention was made with government support under grant numbers HL109015, HL071556, and HL105649 awarded by the National Institutes of Health. The government has certain rights in the invention.

TECHNICAL FIELD

The presently-disclosed subject matter generally relates to compositions and methods for treating cardiomyopathy. In particular, certain embodiments of the presently-disclosed subject matter relate to polypeptides and methods for using the polypeptides to treat cardiomyopathy, including uremic cardiomyopathy.

BACKGROUND

The Na/K-ATPase enzyme is ubiquitously expressed in most eukaryotic cells and helps maintains the trans-membrane ion gradient by pumping $Na^+$ out and $K^+$ into cells. The Na/K-ATPase interacts directly with Src via at least two binding motifs: one being between the CD2 of the α1 subunit and Src SH2; and, the other involving the third cytosolic domain (CD3) and Src kinase domain. The formation of this Na/K-ATPase and Src complex serves as a receptor for ouabain to provoke protein kinase cascades. Specifically, binding of ouabain to Na/K-ATPase will disrupt the latter interaction, and then result in assembly and activation of different pathways including ERK cascades, PLC/PKC pathway and ROS production. Moreover, this interaction keeps Src in an inactive state. Thus, the Na/K-ATPase functions as an endogenous negative Src regulator. See also International Patent Application Nos. WO 2008/054792 and WO 2010/071767, which are both incorporated herein by reference.

Src family kinases are 52-62-kDa membrane-associated nonreceptor tyrosine kinases and they participate in several tyrosine phosphorylation-related signaling pathways in response to various extracellular ligands. Src, for example, contains at least three protein interaction domains. The SH3 domain binds to polyproline motifs and the SH2 domain interacts with the phosphorylated tyrosine residues. The kinase domain reacts with the nucleotide and phosphorylates the substrate. Binding of protein ligands to the SH3 or SH2 domain can activate Src. Proteins that bind with kinase domain of Src were also reported to be capable of regulating Src activity.

It is further appreciated that the Na+/K+-ATPase interacts with Src and Src family kinases to form a functional receptor. Binding of ouabain to this receptor activates Src, which in turn phosphorylates various effectors, resulting in the assembly and activation of different pathways including the Ras/Raf/ERK1/2 and phospholipase C/protein kinase C cascades as well as increases in intracellular $Ca^{2+}$ and cellular ROS production. The activation of these signaling pathways eventually leads to changes in cardiac and renal functions, stimulation of cell proliferation and tissue fibrosis, protection of tissue against ischemia/reperfusion injury, inhibition of cancer cell growth, and more. Src and ROS are also involved in the induction of VEGF expression. While many known Src and Src family kinase inhibitors are developed as ATP analogs that compete for ATP binding to these kinases, such Src inhibitors lack pathway specificity.

The plasmalemmal Na/K-ATPase has a signaling function in addition to and distinct from its pumping function. It has also been demonstrated that this signaling function may amplify oxidants and increase cellular oxidant stress; conversely the blockage of this signal cascade with a designed peptide, pNaKtide attenuate oxidant stress. In particular, pNaKtide antagonizes the cellular generation of reactive oxygen species in response to several stimuli in a dose-dependent manner both in vitro and in vivo. Alternatively, the induction of HO-1 with a variety of agents has also been shown to attenuate oxidant stress. Oxidant stress is a constant feature of both clinical and experimental uremic cardiomyopathy.

Chronic Kidney Disease (CKD) or End Stage Renal Disease (ESRD) is an independent risk factor for cardiovascular mortality, with multiple risk factors which may be specific to CKD. Uremic cardiomyopathy typically involves nonatherosclerotic processes, including characteristic left ventricular hypertrophy and fibrosis. Mortality from cardiovascular diseases (CVD) in patients with ESRD is 10 to 30 times higher than that in the general population. Cardiovascular complications lead in all causes of mortality among patients with CKD, accounting for approximately 50% of deaths. United States Renal Data System (USRDS) data indicate that the mortality rate for patients on dialysis or with ESRD is remarkably higher than that of patients in the same age groups with other major diseases. Targeting future therapies at the underlying cellular mechanisms of uremic cardiomyopathy may reduce the burden of uremic cardiomyopathy in the CKD and ESRD population.

SUMMARY

The presently-disclosed subject matter meets some or all of the above-identified needs, as will become evident to those of ordinary skill in the art after a study of information provided in this document.

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this summary does not list or suggest all possible combinations of such features.

In some embodiments of the presently-disclosed subject matter, methods for treating uremic cardiomyopathy are provided. In some embodiments, a method for treating uremic cardiomyopathy is provided that comprises administering a polypeptide antagonist of a Na/K ATPase/Src receptor complex to a subject in need thereof. In some embodiments, the polypeptide antagonist comprises the sequence of SEQ ID NO: 1, or a fragment, and/or variant thereof. In some embodiments, the polypeptide anatagonist further includes a cell penetrating polypeptide that is encoded by an amino acid sequence selected from the group consisting of SEQ ID NOS: 2-4.

With respect to the administration of the polypeptide antagonists described herein, in some embodiments, the administering step includes oral administration, transdermal administration, administration by inhalation, nasal administration, topical administration, intraaural administration, rectal administration, intravenous administration, intramuscular administration, subcutaneous administration, intravitreous administration, subconjunctival administration, intracameral administration, intraocular administration or combinations thereof to thereby treat the uremic cardiomyopathy.

In some embodiments, the administration of the polypeptides described herein modulate one or more symptoms of the uremic cardiomyopathy and/or modulate one or more of the causes of the uremic cardiomyopathy. In some embodiments, administering the polypeptide antagonist decreases cardiac hypertrophy, diastolic dysfunction, and/or cardiac fibrosis. In some embodiments, administering the polypeptide antagonist decreases oxidant stress, such as what may be measured by a decrease in protein carbonylation. In some embodiments, administering the polypeptide antagonist attenuates c-Src activation, ERK1/2 activation, collagen-1 expression, or combinations thereof.

In some embodiments of the therapeutic methods described herein administering the polypeptide modulates chronic kidney disease-induced related effects. For instance, in some embodiments, administering the polypeptide antagonist reverses chronic kidney disease-induced increases in cardiac anterior wall thickness, posterior wall thickness, and/or relative wall thickness. In some embodiments, administering the polypeptide antagonist reverses chronic kidney disease-induced increases in plasma creatinine levels and BUN levels. In some embodiments, administering the polypeptide antagonist reverses chronic kidney disease-induced increases in left ventricle mass index, increases the ratio of heart weight/body weight, decreases cardiac fibrosis, or combinations thereof.

In further embodiments of the methods for treating uremic cardiomyopathy described herein administering the polypeptide antagonist attenuates profound anemia. In some embodiments, administering the polypeptide antagonist decreases cardiac fibrosis. In some embodiments, administering the polypeptide reduces an expression level of an oxidant stress marker, such as protein carbonylation. In some embodiments, administering the polypeptide antagonist reduces myocardial perfusion index (MPI).

Further provided, in some embodiments of the presently-disclosed subject matter, are methods for treating anemia. In some embodiments, a method for treating anemia is provided that comprises administering a polypeptide antagonist of a Na/K ATPase/Src receptor complex to a subject in need thereof. In some embodiments, after adminstration of the polypeptide, hematocrit in the subject is increased. In some embodiments, the subject has kidney disease. In some embodiments, the anemia is chronic kidney disease-induced anemia.

Further features and advantages of the presently-disclosed subject matter will become evident to those of ordinary skill in the art after a study of the description, figures, and non-limiting examples in this document.

BRIEF DESCRIPTION OF THE DRAWINGS

In FIG. 3A, , p<0.01, vs. Sham; $$, p<0.01 vs. PNx. In FIG. 3B, , p<0.01, vs. Sham; $$, p<0.01 vs. PNx.

FIG. 5A shows representative images of Sirius red cardiac histology (fast green staining as counterstain), and data analyzed with image J and quantified for Sirius red staining. For histology analysis in FIG. 5A, 5 spots per section (3 sections×5 slides per sample) were randomly selected and subjected to analysis using the thresholding function in Image J. FIG. 5B shows collagen-1 expression determined with western blot on homogenates from left ventricles (representative blots above quantified data), n=10 mice per group. FIG. 5C shows representative western blot and data analysis graphs of HO-1 expression on left ventricular homogenates (n=6-8 mice per group). FIG. 5D shows c-Src activation (expressed as pY418 c-Src/total c-Src) measured with western blot on left ventricular homogenates (n=10 mice per group). FIG. 5E shows ERK1/2 activation (expressed as phosphor-ERK/total total ERK) measured with western blot on left ventricular homogenates (n=6-8 mice per group). Value was expressed as Mean±SEM. **, p<0.01 vs. Sham alone; $$, p<0.01 vs. PNx alone.

BRIEF DESCRIPTION OF THE SEQUENCE LISTING

Figure 1A:
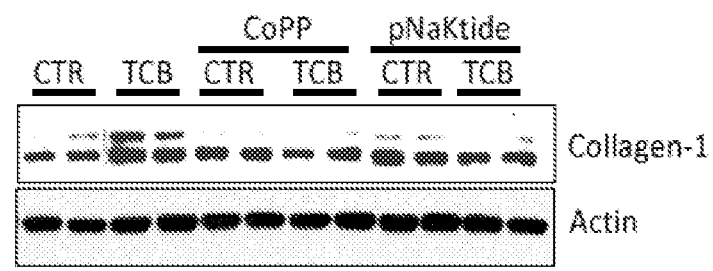
FIGS. 1A-1E include images and graphs showing the effect of telecinobufagin (TCB), induction of hemeoxygenase-1 (HO-1) with cobalt protoporphyrin (CoPP), and blockade of Na/K-ATPase signaling with pNaKtide on murine cardiac fibroblasts, where primary cultures of C57BL/6 mouse cardiac fibroblasts were used for the in vitro studies. The effects of TCB (100 nM), CoPP (5 μM, 24 h) and pNaKtide (1 μM, 1 h) on (FIG. 1A) collagen-1 (n=6-8), (FIG. 1B) c-Src activation (n=6-8), (FIG. 1C) ERK1/2 activation (n=6-8), (FIG. 1D) protein carbonylation (n=6), and (FIG. 1E) HO-1 expression (n=6-8) were analyzed. Collagen-1 and HO-1 were determined after 24 hours of treatment whereas c-Src activation (expressed as pY418 c-Src/total c-Src), ERK1/2 activation (expressed as phosphor-ERK/total ERK), and protein carbonylation were assessed at 1 hour of treatment. For protein carbonylation assay, the Ponceau S stained gel was used for a loading control ** p<0.01 vs control; $$ p<0.01 vs. TCB alone.
Figure 1A:
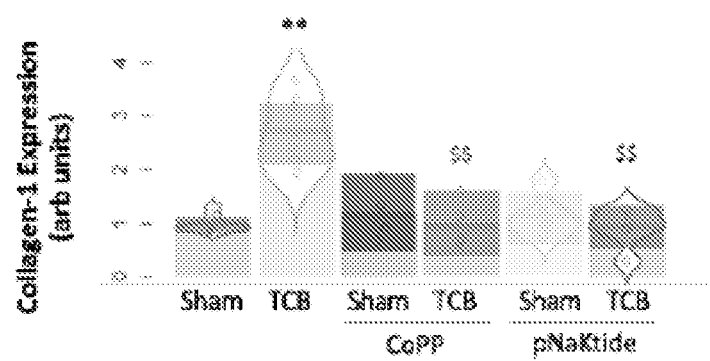

The following is a brief description of the Sequence Listing that is attached hereto and is hereby incorporated by reference in its entirety.

SEQ ID NO: 1 is an amino acid sequence of an embodiment of a polypeptide in accordance with the presently-disclosed subject matter (NaKtide);

SEQ ID NO: 2 is an amino acid sequence encoding a TAT cell penetrating peptide;

SEQ ID NO: 3 is an amino acid sequence encoding a penetratin (AP) cell penetrating peptide; and SEQ ID NO: 4 is an amino acid sequence encoding the N-terminal poly-lysine domain of the α1 subunit of Na/K-ATPase (AlN); and SEQ ID NO: 5 is another amino acid sequence of an embodiment of a polypeptide in accordance with the presently-disclosed subject matte (pNaKtide).

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding, and no unnecessary limitations are to be understood therefrom.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

Although any methods, devices, and materials similar or equivalent to those described herein can be used in the practice or testing of the presently-disclosed subject matter, representative methods, devices, and materials are described herein.

The present application can "comprise" (open ended) or "consist essentially of" the components of the present invention as well as other ingredients or elements described herein. As used herein, "comprising" is open ended and means the elements recited, or their equivalent in structure or function, plus any other element or elements which are not recited. The terms "having" and "including" are also to be construed as open ended unless the context suggests otherwise.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

The presently-disclosed subject matter includes compositions and methods for treating cardiomyopathy. The term "uremic cardiomyopathy" as used herein is used to refer to cardiovascular manifestations of ESRD or CKD, and which can be characterized by left ventricular hypertrophy (LVH), left ventricular dilatations and left ventricular systolic and diastolic dysfunction, which are each prevalent cardiovascular abnormalities that arise as a manifestation of uremic cardiomyopathy.

In some instances, cardiomyopathy itself can be characterized by one or more levels of wall thickness (anterior, posterior and relative wall thickness), left ventricular mass index (LVMI), heart weight/body weight ratio, cardiac fibrosis as assessed by histology, collagen 1-expression, cardiac c-Src activation, oxidant stress as assessed by protein carbonylation, profound anemia, decreases in hematocrit, increases in plasma creatinine, cystatin C, BUN, cardiac hypertrophy, cardiac fibrosis, and/or MPI, an index of systolic and diastolic function.

As disclosed herein, however, it has been surprisingly discovered that the administration of a polypeptide antagonist of a Na/K ATPase/Src receptor complex in a patient with uremic cardiomyopathy can result in improvement of phenotypical changes characteristic of uremic cardiomyopathy. In particular, it was observed that improvement of oxidant stress with administration of a polypeptide antagonist of a Na/K ATPase/Src receptor complex resulted in improved left ventricular diastolic function and decreased hypertrophy, less cardiac fibrosis, and less evidence for Na/K-ATPase signaling and ROS stress. In some embodiments, the administration of a polypeptide antagonist of a Na/K ATPase/Src receptor complex in a patient with uremic cardiomyopathy thus results in improvement of oxidant stress, increased left ventricular diastolic function and decreased hypertrophy, reduced cardiac fibrosis, and/or amelioration of profound anemia.

Embodiments of the present compositions include a polypeptide that can be utilized to treat cardiomyopathy. The polypeptide can include a polypeptide that inhibits the receptor function of the Na/K-ATPase and Src complex. In some embodiments the polypeptide is an antagonist for the receptor function of the Na/K-ATPase and Src complex. The terms "polypeptide," "protein," and "peptide" are used interchangeably herein to refer to a polymer of the protein amino acids regardless of its size or function. The terms "protein," "polypeptide," and "peptide" are used interchangeably herein to also refer to a gene product, homologs, orthologs, paralogs, fragments, any protease derived peptide (fragment), and other equivalents, variants, and analogs of a polymer of amino acids.

In some embodiments, the polypeptides are comprised of the sequence of SEQ ID NO: 1 (NaKtide), or fragments, and/or variants thereof. The terms "polypeptide fragment" or "fragment" when used in reference to such a reference polypeptide, refers to a polypeptide in which amino acid residues are deleted as compared to the reference polypeptide itself, but where the remaining amino acid sequence is identical to the corresponding positions in the reference polypeptide. Such deletions may occur at the amino-terminus of the reference polypeptide, the carboxy-terminus of the reference polypeptide, or both. Polypeptide fragments can also be inclusive of "functional fragments," in which case the fragment retains some or all of the activity of the reference polypeptide.

The term "variant," as used herein, refers to an amino acid sequence that is different from the reference polypeptide by one or more amino acids. In some embodiments, a variant polypeptide may differ from a reference polypeptide by one or more amino acid substitutions. For example a NaKtide polypeptide variant can differ from the NaKtide polypeptide of SEQ ID NO: 1 by one or more amino acid substitutions, i.e., mutations. In this regard, polypeptide variants comprising combinations of two or more mutations can respectively be referred to as double mutants, triple mutants, and so forth. It will be recognized that certain mutations can result in a notable change in function of a polypeptide, while other mutations will result in little to no notable change in function of the polypeptide.

In some embodiments, the present polypeptides include polypeptides that share at least 75% homology with the pNaKtide polypeptide of SEQ ID NO: 1. In some embodiments, the polypeptides share at least 85% homology with the NaKtide polypeptide of SEQ ID NO: 1. In some embodiments, the polypeptides share at least 90% homology with the NaKtide polypeptide of SEQ ID NO: 1. In some embodiments, the polypeptides share at least 95% homology with the NaKtide polypeptide of SEQ ID NO: 1.

"Percent identity," or "percent homology" when used herein to describe to an amino acid sequence or a nucleic acid sequence, relative to a reference sequence, can be determined using the formula described by Karlin and Altschul (Proc. Natl. Acad. Sci. USA 87: 2264-2268, 1990, modified as in Proc. Natl. Acad. Sci. USA 90:5873-5877, 1993). Such a formula is incorporated into the basic local alignment search tool (BLAST) programs of Altschul et al. (J. Mol. Biol. 215: 403-410, 1990).

Embodiments of the present polypeptides can further comprise one or more leader sequences, and in some embodiments the leader sequences including, but not limited to, cell penetrating peptides (CPPs). The term "cell penetrating peptide" (CPP) is used herein to generally refer to short peptides that can facilitate or that assist in facilitating the transport of molecular cargo across plasma membranes found in a cell. In some instances, the molecular cargo includes another polypeptide, such as the polypeptides described herein. Of course, the cell penetrating peptides can be conjugated to the molecular cargo (e.g., polypeptide) via any number of means, including covalent bonds and/or non-covalent bonds. In a number of instances, however, such cell penetrating peptides will often include a relatively high concentration of positively-charged amino acids, such as lysine and arginine, and will have a sequence that contains an alternating pattern of charged (polar) and non-charged amino acids.

In some embodiments of the presently-disclosed subject matter, an exemplary leader sequence or cell-penetrating peptide can include the trans-activating transcriptional activator (TAT) cell penetrating peptide, which is represented by the sequence of SEQ ID NO: 2 and which when combined with the NaKtide peptide of sequence of SEQ ID NO: 1 generates a peptide designated pNaKtide referred to herein below. Another exemplary leader sequence includes penetratin (AP), which is represented by the sequence of SEQ ID NO: 3. Yet another exemplary leader sequence includes an amino acid sequence encoding the N-terminal poly-lysine domain of the α1 subunit of Na/K-ATPase (AlN), which is represented by the sequence of SEQ ID NO: 4. Those of ordinary skill will appreciate though that other leader sequences, including other cell penetrating peptides, can also be used in conjunction with the presently-disclosed polypeptides. In some embodiments, a polypeptide including a leader sequence, such as a cell penetrating peptide, attached to the NaKtide sequence of SEQ ID NO: 1 is referred to herein as a pNaKtide (e.g., SEQ ID NO: 5; GRKKRRQRRRPPQSATWLALSRIAGLCNRAVFQ, which includes the TAT cell penetrating peptide of SEQ ID NO: 2 fused to the NaKtide sequence of SEQ ID NO: 1).

The presently-disclosed subject matter further includes and makes use of pharmaceutical compositions comprising the poly peptides described herein as well as a pharmaceutically-acceptable carrier. Indeed, when referring to certain embodiments herein, the terms "polypeptide" and/or "composition" may or may not be used to refer to a pharmaceutical composition that includes the polypeptide.

The term "pharmaceutically-acceptable carrier" as used herein refers to sterile aqueous or nonaqueous solutions, dispersions, suspensions, or emulsions, as well as sterile powders for reconstitution into sterile injectable solutions or dispersions just prior to use. Proper fluidity can be maintained, for example, by the use of coating materials such as lecithin, by the maintenance of the required particle size in the case of dispersions and by the use of surfactants. These compositions can also contain adjuvants, such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride, and the like.

Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of polypeptide to biodegradable polymer and the nature of the particular biodegradable polymer employed, the rate of polypeptide release can be controlled. Depot injectable formulations can also be prepared by entrapping the polypeptide in liposomes or microemulsions, which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose.

Suitable formulations can further include aqueous and non-aqueous sterile injection solutions that can contain antioxidants, buffers, bacteriostats, bactericidal antibiotics, and solutes that render the formulation isotonic with the bodily fluids of the intended recipient; and aqueous and non-aqueous sterile suspensions, which can include suspending agents and thickening agents.

The compositions can also take forms such as suspensions, solutions, or emulsions in oily or aqueous vehicles, and can contain formulatory agents such as suspending, stabilizing and/or dispersing agents. Alternatively, the polypeptides can be in powder form for constitution with a suitable vehicle, e.g., sterile pyrogen-free water, before use.

The formulations can be presented in unit-dose or multidose containers, for example sealed ampoules and vials, and can be stored in a frozen or freeze-dried (lyophilized) condition requiring only the addition of sterile liquid carrier immediately prior to use.

For oral administration, the compositions can take the form of, for example, tablets or capsules prepared by a conventional technique with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycollate); or wetting agents (e.g., sodium lauryl sulphate). The tablets can be coated by methods known in the art.

Liquid preparations for oral administration can take the form of, for example, solutions, syrups or suspensions, or they can be presented as a dry product for constitution with water or other suitable vehicle before use. Such liquid preparations can be prepared by conventional techniques with pharmaceutically acceptable additives such as suspending agents (e.g., sorbitol syrup, cellulose derivatives or hydrogenated edible fats); emulsifying agents (e.g. lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate. Preparations for oral administration can be suitably formulated to give controlled release of the active compound. For buccal administration, the compositions can take the form of tablets or lozenges formulated in a conventional manner.

The compositions can also be formulated as a preparation for implantation or injection. Thus, for example, the compounds can be formulated with suitable polymeric or hydrophobic materials (e.g., as an emulsion in an acceptable oil) or ion exchange resins, or as sparingly soluble derivatives (e.g., as a sparingly soluble salt). The compounds can also be formulated in rectal compositions, creams or lotions, or transdermal patches.

As described herein, the presently-disclosed subject matter further includes methods for treating cardiomyopathies with a polypeptide. Some embodiments of methods include administering one of the presently-disclosed polypeptides to a subject in need thereof. The polypeptide can treat a cardiomyopathy by inhibiting the receptor function of the Na/K-ATPase and Src complex, and in some embodiments the polypeptides inhibit the receptor function by acting as an antagonist of the Na/K-ATPase and Src complex.

The presently-disclosed subject matter further includes methods of treating profound anemia, which is generally present in chronic kidney failure. Treatment of uremic cardiomyopathy can also be characterized by a decrease in profound anemia. Through the course and development of the presently-disclosed subject matter, it was surprisingly found that treatments with pNaKtide increased the hematocrit in a dose-dependent manner, and profound anemia caused by nephrectomy was substantially alleviated. In some embodiments, a method for treating anemia is provided comprising administering a polypeptide antagonist of a Na/K ATPase/Src receptor complex to a subject in need thereof. In some embodiments, such treatment increases hematocrit. In some embodiments, the patient in need of treatment for anemia has kidney disease.

Anemia refers to an absolute reduction of the total number of circulating red blood cells (RBCs), and is considered when one or more of the following are decreased: hemoglobin, hematocrit, or red blood cell (RBC) count. Hematocrit is the percentage of the blood volume that is occupied by red blood cells or erythrocytes.

As used herein, the terms "inhibiting," "inhibition," "reverse," "attenuate" and the like do not necessarily refer to the ability to completely inactivate all target biological activity in all cases. Rather, the skilled artisan will understand that those terms refer to decreasing biological activity of a target, such as can occur when a ligand binds a site of the target, a protein in a biochemical pathway of the target is blocked, a non-native complexes with a target, or the like. Such decrease in biological activity can be determined relative to a control, wherein the control can be representative of, for example, an environment in which an inhibitor is not administered. For example, in some embodiments, a decrease in activity relative to a control can be about a 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% decrease.

In this regard, the terms "treatment" or "treating" refer to the medical management of a subject with the intent to cure, ameliorate, or stabilize a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; and supportive treatment, that is, treatment employed to supplement another therapy directed toward the improvement of the associated disease, pathological condition, or disorder.

The treatment of a cardiomyopathy can be measured and quantified in several different ways. In some embodiments, treatment of cardiomyopathy can be measured and quantified by, among other things, amelioration of collagen-1 increased expression, reduction in the activation of c-Src, ERK1/2, and protein carbonylation, or a combination thereof. Alternatively or additionally, treatment of cardiomyopathy can be characterized by attenuation of cardiac hypertrophy, diastolic dysfunctions, relative wall thickness, the ratio of heart weight/body weight, cardiac fibrosis, oxidant stress, and combinations thereof. In some embodiments, uremic cardiomyopathy can be reversed. Treatment of cardiomyopathy can also be characterized by a decrease in profound anemia, in other instances, decreased and/or inhibited Myocardial Performance Index (MPI), plasma creatinine and blood urea nitrogen (BUN) levels. In some embodiments, the increases and/or decreases described herein can be in reference to a control subject having a cardiomyopathy and that has not been treated with one of the presently-disclosed polypeptides. In other embodiments, the increases and/or decreases described herein can be in reference to a baseline measurement of the subject prior to treatment with one of the presently-discloses polypeptides. Measurement of such increases or decreases, including techniques for the measurements, are known to those of ordinary skill in the art.

In this regard, the term "administering" is not particularly limited and refers to any method of providing a polypeptide and/or pharmaceutical composition thereof to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, subcutaneous administration, intravitreous administration, intracameral (into anterior chamber) administration, subretinal administration, sub-Tenon's administration, peribulbar administration, administration via topical eye drops, and the like. Administration can be continuous or intermittent. In various aspects, a preparation can be administered therapeutically; that is, administered to treat an existing disease or condition.

The present methods can be performed on a wide variety of subjects. Indeed, the term "subject" as used herein is not particularly limited. The term "subject" is inclusive of vertebrates, such as mammals, and the term "subject" can include human and veterinary subjects. Thus, the subject of the herein disclosed methods can be a human, non-human primate, horse, pig, rabbit, dog, sheep, goat, cow, cat, guinea pig, rodent, or the like. The term does not denote a particular age or sex. Thus, adult and newborn subjects, as well as fetuses, whether male or female, are intended to be covered.

The presently-disclosed subject matter is further illustrated by the following specific but non-limiting examples.

EXAMPLES

Na/K-ATPase signaling may regulate cardiac fibrosis, so it was determined whether attenuation of oxidant stress by antagonism of Na/K-ATPase oxidant amplification with pNaKtide might affect experimental uremic cardiomyopathy induced by partial nephrectomy (PNx). As a control, attenuation of oxidant stress by upregulation of hemeoxygenase-1 (HO-1) using cobalt protoporphyrin (CoPP) was also studied.

As described in detail below, it was observed that PNx induced the development of cardiac morphological and biochemical changes consistent with human uremic cardiomyopathy. It was found that both inhibition of Na/K-ATPase signaling with pNaKtide and induction of HO-1 with CoPP both markedly attenuated the development of phenotypical features of uremic cardiomyopathy including cardiac hypertrophy and diastolic dysfunction determined with echocardiography and cardiac fibrosis assessed with both histological and biochemical techniques. In vitro studies confirmed that both CoPP and pNaKtide decreased telecinobufagin (TCB, a cardiotonic steroid) stimulated type I collagen production and cellular oxidant stress in C57BL/6 mouse primary cardiac fibroblast cells. In a reversal study, administration of pNaKtide after the induction of uremic cardiomyopathy reversed many of the phenotypical features. Addressing oxidant stress by HO-1 induction or attenuation of Na/K-ATPase oxidant amplification may be an effective strategy for clinical therapy of this disorder.

The following examples thus demonstrate that pNaKtide can decrease cardiac hypertrophy and diastolic dysfunctions in a renal failure mouse model. The increase in collagen-1 expression in the left ventricle was reduced, cardiac fibrosis was attenuated, cardiac hypertrophy and diastolic dysfunctions caused by nephrectomy were also attenuated. Surprisingly, profound anemia caused by nephrectomy was substantially alleviated and the increase in ratio of heart weight to body weight was decreased. Moreover, when mice were allowed to develop uremic cardiomyopathy, some indicators were reversed in a dose dependent manner. The examples show that pNaKtide reduces several factors indicative of oxidant stress, cardiac hypertrophy and diastolic dysfunctions, and is potent and effective in blocking and reversing uremic cardiomyopathy.

Materials and Methods

Experimental designs: Male C57BL/6 10-12 weeks were purchased from Hill Top Laboratories and housed in pathogen free animal facility in designated rooms equipped with cages that supply purified air under a 12 hour light/dark cycle. Food and water were supplied ad libitum. Animal protocol was approved by the Marshall University Institutional Animal Care and Use Committee. The number of animals in each group was determined by Power analysis using the following assumptions derived from a previous study with mice, with variance of 0.2 within the groups, power of 0.80, and alpha error of 0.05.

Effects of CoPP and pNaKtide on PNx-induced cardiomyopathy: Cobalt protoporphyrin (CoPP, Frontier Scientific, Logan, UT) was used to induct HO-1 expression and pNaKtide was used to block the Na/K-ATPase signaling function. The animals were randomly divided into six groups (10-12 mice per group): (1) Sham surgery (Sham), (2) PNx surgery (PNx), (3) Sham+CoPP (5 mg/kg BW), (4)

PNx+CoPP (5 mg/kg BW), (5) Sham+pNaKtide (25 mg/kg BW), and (6) PNx+pNaKtide (25 mg/kg BW).

Reversal study: At week 4 of post-surgery, the animals were randomly divided into different groups and given pNaKtide (0, 1, 5, 10 and 25 mg/kg BW) 3 times (every other day), and then sacrificed 7 days after first injection of pNaKtide.

Nephrectomy Mouse Model: The PNx model included two-step surgeries. Step-one, the superior and inferior poles of the left kidney were ligated in a manner where approximately only ⅓ of the left kidney mass was left functional. Step-two surgery was operated 7 days later, in which the right kidney was removed. For sham surgery, the two-step surgeries were performed in the same way as in the PNx group, without ligation of left kidney and removal of right kidney. In the first "Effects of CoPP and pNaKtide on PNx-induced cardiomyopathy" study, animals were sacrificed 4 weeks after the step two surgery. In the second "reversal study", animals were given either vehicle or pNaKtide beginning at 4 weeks post-surgery with animals for one week and sacrificed at 5 weeks post-surgery.

Administration of pNaKtide and CoPP: In the "Effects of CoPP and pNaKtide on PNx-induced cardiomyopathy" study, pNaKtide was dissolved in sterile PBS buffer and administrated (25 mg/kg BW) by intraperitoneal injection weekly, starting one week after second step surgery up until the point of sacrificing. CoPP was prepared in Tris-NaOH buffer (25 mM Tris, pH 7.8-8.0) and administered (5 mg/kg BW) by intraperitoneal injection. CoPP injections were given 5 days prior to, and on the day of, surgery, as well as every 5 days thereafter until sacrificing. In the Reversal study, pNaKtide was administered at 0, 1, 5, 10 and 25 mg/kg 3 times a week beginning at the end of week 4 post-surgery and sacrificed at the end of the additional week.

Blood Pressure (BP) measurement: Mice were first conditioned in restrainers for at least five days prior to first BP reading. BP measurements were performed with CODA 8-Channel High Throughput Non-Invasive Blood Pressure system (Kent Scientific, Boston, MA) both one day before step-one surgery, and one day before sacrifice.

Transthoracic Echocardiography: Transthoracic echocardiography was performed 24 hours before sacrifice. Light anesthesia was achieved by continuous inhalation of isoflurane (1.5-2.5%). Mice in supine position were placed on a heating pad to keep the body temperature at 37° C. Body core temperature and ECG for physiological monitoring were obtained and manipulated by using a Visualsonics Mouse Handling Table (11436) and a rectal thermometer. Echocardiographic images were captured using MS400: 18-38 MHz operating frequency MicroScan transducer attached to a Vevo 1100 Imaging System (FUJIFILM VisualSonics Inc.). Warmed echo gel was placed between the probe and shaved chest. B-mode and M-mode images of the heart were obtained from parasternal long axis and short axis. PW Doppler and Color Doppler were obtained from basal short axis. The average values were calculated from at least four consecutive cardiac cycles. Left-ventricular end-diastolic area (EDA), end-systolic area (ESA), as well as main pulmonary artery diameter was measured from B-mode. End-diastolic diameters (EDD), end-systolic diameters (ESD), as well as anterior and posterior wall thickness (AWT & PWT) were captured from M-mode. Isovolumic contraction and relaxation time (IVCT & IVRT), ejection time (ET), as well as pulmonary velocity time integral (VTI) were obtained from PW and color Doppler. In addition, the following parameters were calculated with the equation below: myocardial performance index (MPI)=(IVCT+IVRT)/ET, relative wall thickness (RWT)=(PWT+AWT)/EDD, cardiac output (CO)=SV×HR/1000, fractional shortening (FS)=(EDD−ESD)/EDD, ejection fraction (EF)=(EDV−ESV)/EDV.

Sirius Red/Fast Green staining: Histology staining for collagen fiber was performed on tissues harvested with Sirius Red/Fast Green Collagen Staining solutions (Sigma-Aldrich) according to the manufacturer's protocol. Tissues preparation, fixation, and data analysis were conducted as previously described.

Western Blotting Analysis: Cardiac (left ventricle) tissue samples and cardiac fibroblast homogenates were prepared and analyzed as was previously described for collagen-1 and other proteins. Assessment of protein carbonylation and activation of c-Src and ERK1/2 was performed as was described previously. Multiple exposures were analyzed to assure that the signals were within the linear range of the film. The signal density was determined using NIH ImageJ 1.48v software. Polyclonal antibody against type I collagen was from Southern Biotech (Birmingham, AL). Polyclonal anti-Src [pY418] phosphospecific antibody was from Invitrogen (Camarillo, CA). Monoclonal antibody against total c-Src was from Santa Cruz (Santa Cruz, CA). 2,4-dinitrophenylhydrazine (DNPH) and antibody against 2,4-dinitrophenyl (DNP) hydrazone derivatives were from Sigma-Aldrich.

Experimental design for in vitro experiment: C57BL/6 mouse primary cardiac fibroblast cells (purchased from Cell Biologics, Inc., Chicago, IL) were resuspended in complete fibroblast medium with supplements and 10% FBS (Cell Biologics, Inc.). The cultures were maintained at 37° C. in a 5% $CO_2$ incubator and the medium was changed after 48 h and every 2-3 days thereafter. Cardiac fibroblast cells (passage 3-4) were grown until over confluent and were serum-starved (with 1% FBS) overnight before being used for the experiments. Cells were treated with or without TCB (100 nM) to determine procollagen-1 and HO-1 expression (24 h treatment), and c-Src activation and protein carbonylation (1 h treatment). To determine the effect of HO-1 induction and pNaKtide, some cells were pre-treated with CoPP (5 μM, 24 h) or pNaKtide (1 μM, 1 h) before TCB treatment.

Measurement of plasma cystatin C, creatinine and blood urea nitrogen (BUN): Mouse cystatin C ELISA kit and mouse creatinine kit were obtained from Crystal Chem. Inc. (Downers Grove, IL). Mouse BUN ELISA kit was obtained from MyBioSource Inc (San Diego, CA). The measurements were performed following manufacturers' instructions. Each sample was tested in duplicate.

Figure 10:
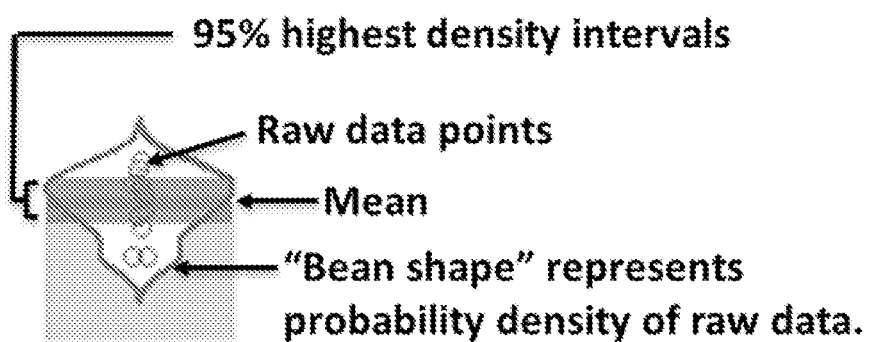
FIG. 10 is a schematic diagram describing the representation of data in the graphs included herein, where data were presented with mean, 95% of highest density intervals (HDIs), raw data points, and probability density of raw data (the "bean" shape).

Statistical analysis: Data were tested for normality and then subjected to parametric analysis. When more than two groups were compared, one-way ANOVA was performed prior to comparison of individual groups, and the post-hoc t-tests were adjusted for multiple comparisons using the Tukey-Kramer correction. Statistical significance was reported at the $P<0.05$ and $P<0.01$ levels. Statistical analyses were performed with the IDE RStudio for the R (version 3.2.5) software. A pirate plot was used to form graphs, in which the raw data points, full densities of each group, and Baynesian 95% Highest Density Intervals (HDIs) are plotted. The HDIs were calculated using the BEST package in R. Values are given as mean±SEM in Table 1 and 2. In graph presentation, data were presented with mean, 95% of highest density intervals (HDIs), raw data points, and probability density of raw data (the "bean" shape, see, e.g., FIG. 10).

Figure 1B:
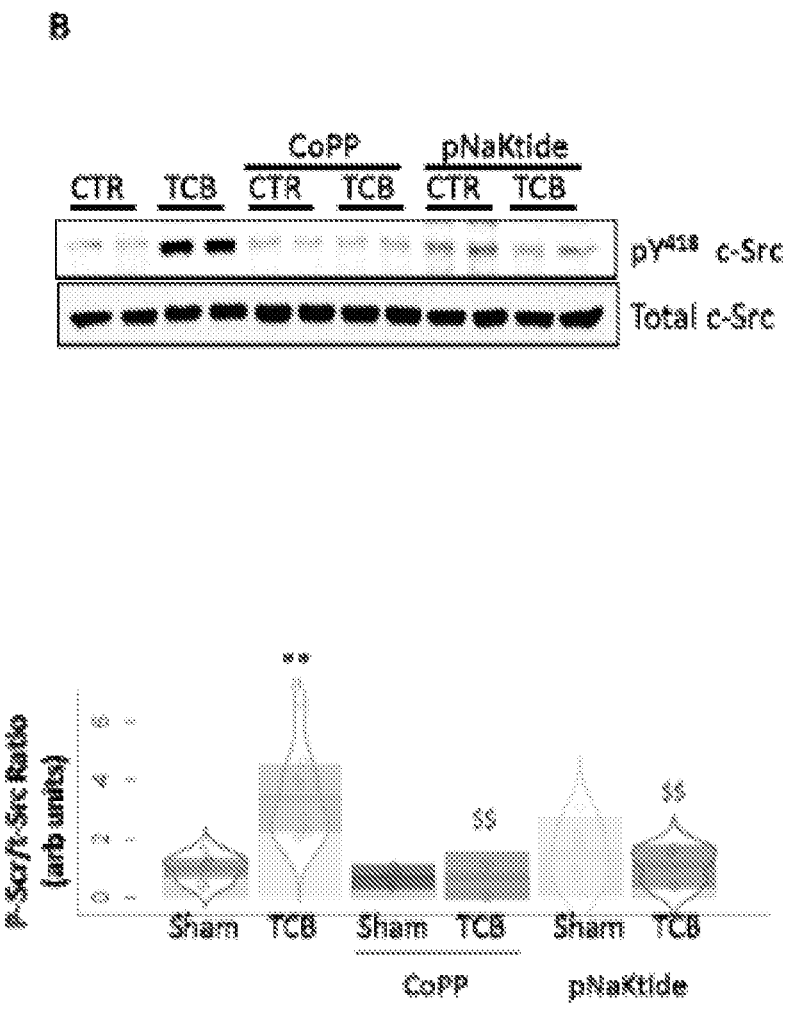
Figure 1C:
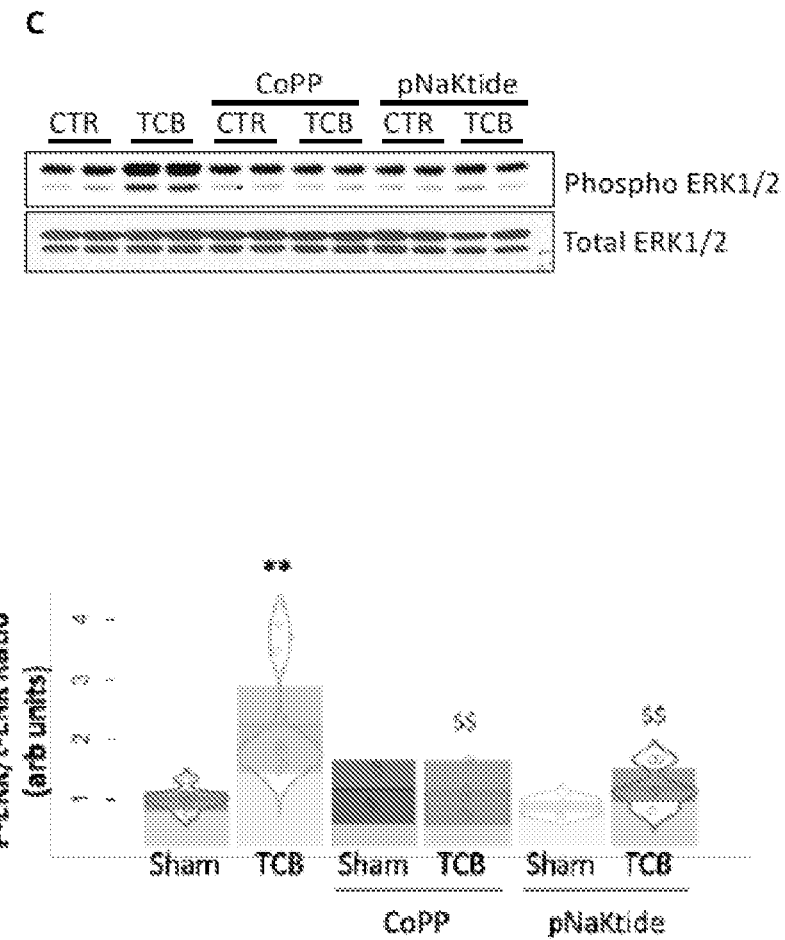
Figure 1D:
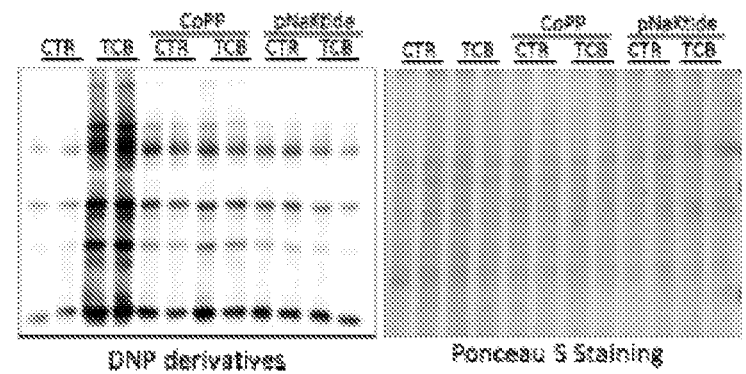
Figure 1D:
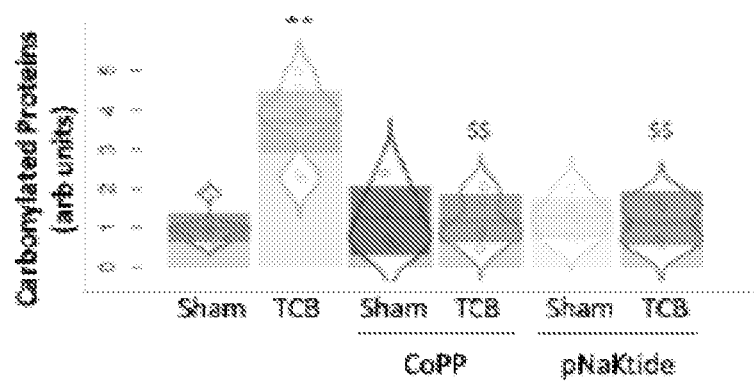
Figure 1E:
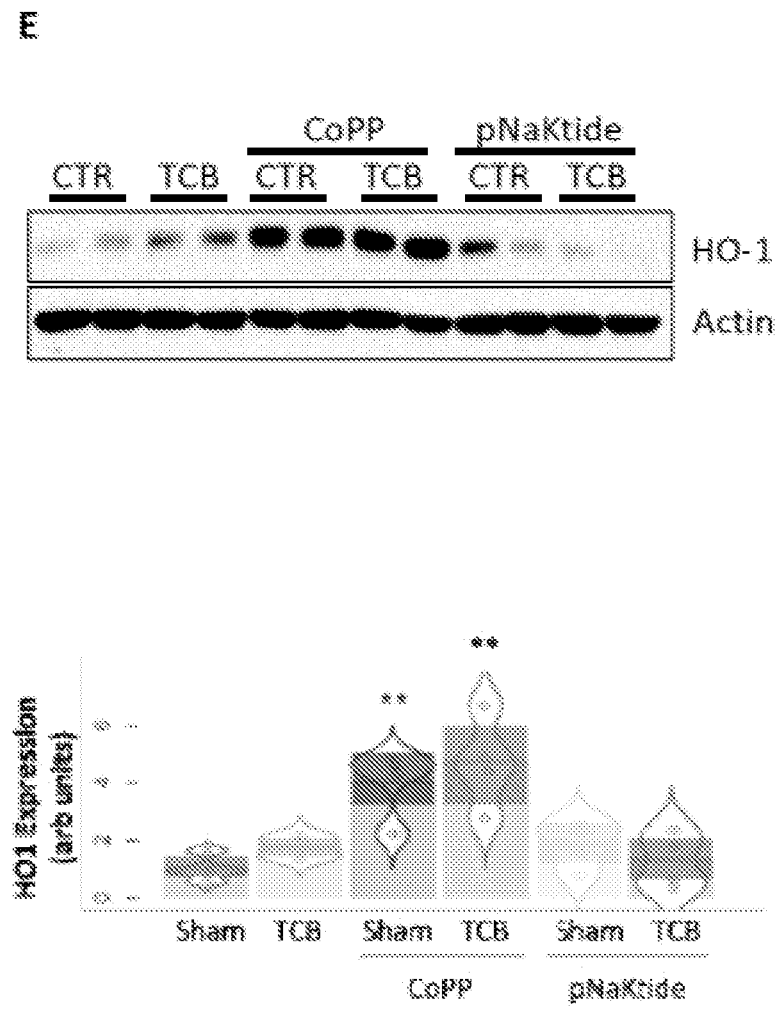

Example 1—Effect of Telecinobufagin (TCB) and pNaKtide on Collagen Production and Signaling in C57BL/6 Mouse Primary Cardiac Fibroblast Cells It was found that the TCB (100 nM, 24 h) induced increases in type I collagen (collagen-1) expression (FIG. 1A, $p<0.01$ vs control). Induction of HO-1 with CoPP (5 µM, 24 h) and inhibition of Na/K-ATPase signaling with pNaKtide (1 µM, 1 h) did not significantly affect collagen-1 expression at baseline but significantly ameliorated TCB induced increases (FIG. 1A, both $p<0.01$ vs TCB alone). TCB also induced activation of c-Src (FIG. 1B), ERK1/2 (FIG. 1C), and protein carbonylation (FIG. 1D), which were also attenuated by CoPP or pNaKtide. Although TCB treatment increased HO-1 expression, the effects of CoPP on HO-1 induction were considerably greater (FIG. 1E). The administration of pNaKtide had a small effect on HO-1 expression which did not attain statistical significance and appeared to be substantially less than that achieved by CoPP (FIG. 1E).

Example 2—Effect of pNaKtide and CoPP on Cardiac Function and Hemodynamics

Figure 2:
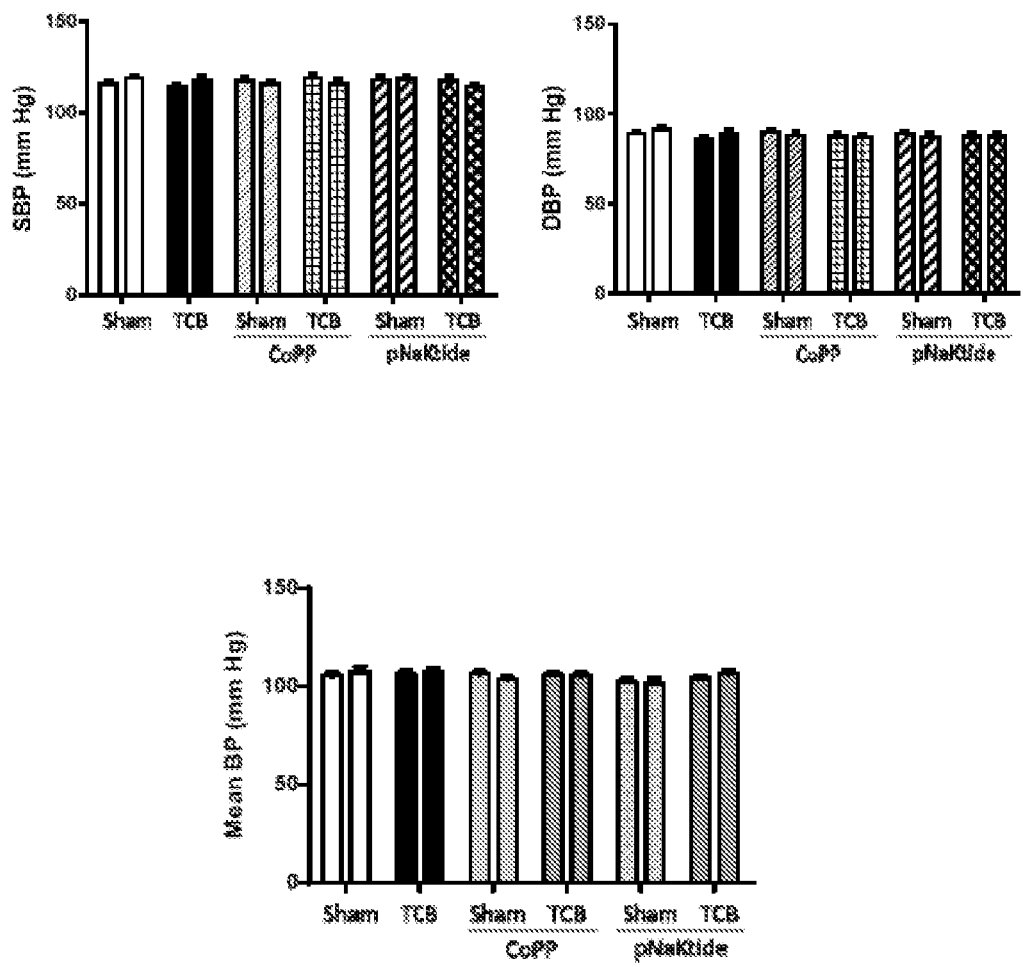
FIG. 2 includes graphs showing blood pressure measurements in mice subject to a partial nephrectomy (PNx).
Figure 3A:
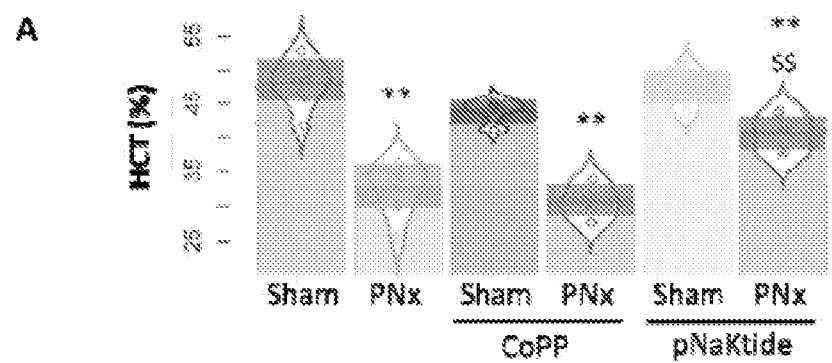
FIGS. 3A-3B show the effect of CoPP and pNaKtide treatment on hematocrit levels and heart weight to body weight ratio in PNx mice.
Figure 3B:
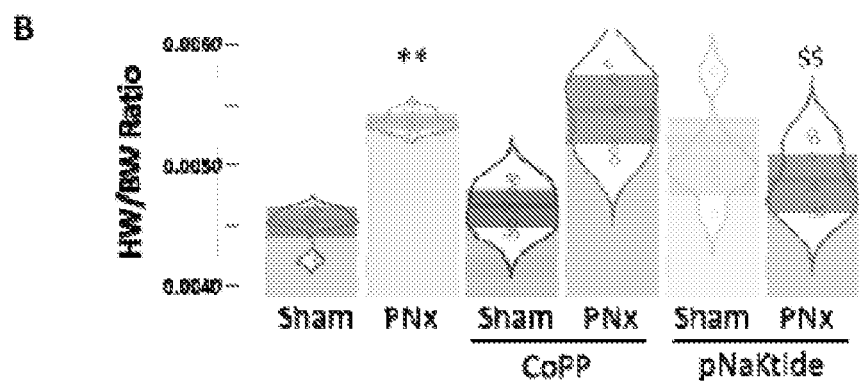
Figure 4A:
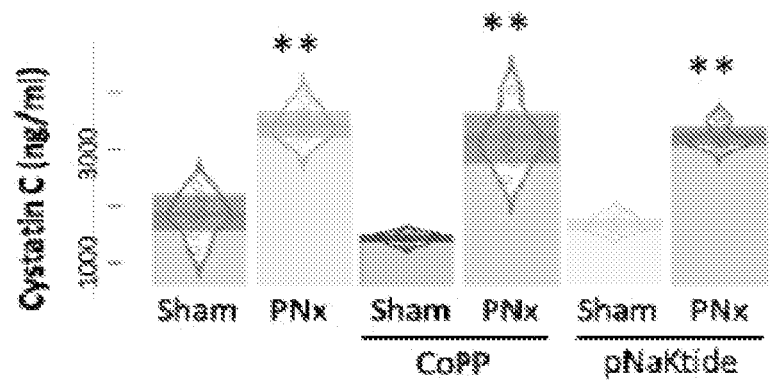
FIGS. 4A-4C are graphs showing the impairment of renal function by the PNx model as assessed by plasma (FIG. 4A) cystatin C, (FIG. 4B) creatinine, and (FIG. 4C) blood urea nitrogen (BUN).
Figure 4B:
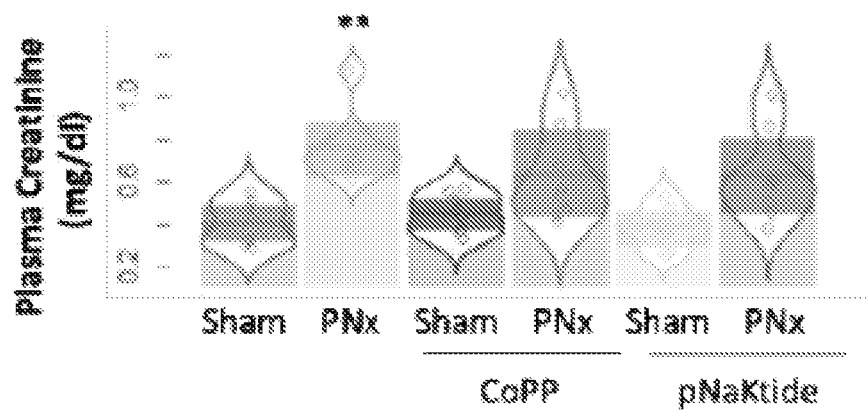
Figure 4C:
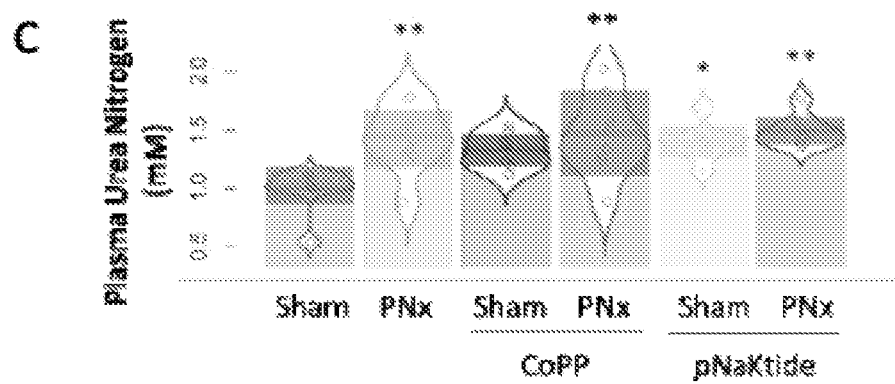

PNx resulted in the consistent development of cardiac hypertrophy and diastolic dysfunction as assessed by echocardiographic methods, summarized in Table 1. Specifically, PNx increased the relative wall thickness (RWT) and myocardial performance index (MPI), and these increases were significantly attenuated by either pNaKtide or CoPP treatment (Table 1). As this model of experimental renal failure does not induce hypertension in this mouse strain, similar BP measurements are shown in FIG. 2. Neither pNaKtide nor CoPP had significant effects measured with echocardiography in sham treated mice (Table 1). Interestingly, PNx induced profound anemia which was substantially alleviated by concomitant administration of pNaKtide but not CoPP (FIG. 3A). The increase in heart weight/body weight ratio with PNx was also markedly attenuated by pNaKtide but not CoPP (FIG. 3B). Impairment of renal function by this model as assessed by plasma cystatin C, creatinine, and BUN was noted in the PNx group, but neither CoPP nor pNaKtide effected significant changes in these measurements (FIGS. 4A-4C).

TABLE 1

Summary of transthoracic echocardiography.

| Variable | Sham (n = 18) | PNX (n = 21) | Sham + CoPP (n = 12) | PNX + CoPP (n = 15) | Sham + pNaktide (n = 13) | PNX + pNaktide (n = 14) |
|---|---|---|---|---|---|---|
| BW, g | 26.4 ± 0.5 | 26.1 ± 0.4 | 28.4 ± 0.6 | 24.6 ± 0.6 | 28.1 ± 0.5 | 25.6 ± 0.6 |
| HR, beat/min | 429 ± 5 | 432 ± 18 | 425 ± 8 | 453 ± 11 | 442 ± 9 | 414 ± 10 |
| EDA, $mm^2$ | 26.3 ± 0.3 | 26.3 ± 0.5 | 28.4 ± 0.5 | 27.2 ± 0.6 | 29.6 ± 0.6 | 27.9 ± 0.5$^\$$ |
| ESA, $mm^2$ | 17.1 ± 0.3 | 17.5 ± 0.5 | 18.3 ± 0.5 | 19.0 ± 0.1 | 20.9 ± 0.5 | 20.5 ± 0.5$^{\$\$}$ |
| EDD, mm | 4.4 ± 0.1 | 4.4 ± 0.4 | 4.5 ± 0.04 | 4.4 ± 0.1 | 4.6 ± 0.1 | 4.5 ± 0.5 |
| ESD, mm | 3.3 ± 0.1 | 3.3 ± 0.1 | 3.4 ± 0.1 | 3.2 ± 0.1 | 3.5 ± 0.1 | 3.4 ± 0.1 |
| PWT, mm | 0.59 ± 0.01 | 0.68 ± 0.01** | 0.60 ± 0.01 | 0.59 ± 0.02$^{\$\$}$ | 0.62 ± 0.02 | 0.59 ± 0.01$^{\$\$}$ |
| AWT, mm | 0.68 ± 0.01 | 0.77 ± 0.01** | 0.67 ± 0.02 | 0.65 ± 0.01$^{\$\$}$ | 0.69 ± 0.01 | 0.70 ± 0.01$^{\$\$}$ |
| ET, msec | 47 ± 0.6 | 46 ± 0.8 | 48 ± 1.0 | 44 ± 1.0 | 48 ± 0.8 | 48 ± 1.1 |
| IVCT + IVRT, msec | 20 ± 0.5 | 24 ± 0.7** | 19 ± 0.8 | 21 ± 0.7$^{\$\$}$ | 22 ± 0.8 | 22 ± 0.7$^\$$ |
| PaVTI | 27.52 ± 0.7 | 27.0 ± 0.5 | 30.6 ± 1.0 | 29.9 ± 0.5$^\$$ | 28.8 ± 1.1 | 26.2 ± 0.7 |
| PaD, mm | 1.0 ± 0.01 | 1.0 ± 0.01 | 1.0 ± 0.02 | 1.0 ± 0.02 | 1.0 ± 0.02 | 1.0 ± 0.07 |
| RWT | 0.29 ± 0.01 | 0.33 ± 0.01** | 0.28 ± 0.01 | 0.28 ± 0.01$^{\$\$}$ | 0.29 ± 0.01 | 0.29 ± 0.01$^{\$\$}$ |
| MPI | 0.43 ± 0.01 | 0.51 ± 0.01** | 0.40 ± 0.01 | 0.46 ± 0.01$^{\$\$}$ | 0.46 ± 0.02 | 0.46 ± 0.01$^{\$\$}$ |
| FS, % | 25.8 ± 0.8 | 25.5 ± 1.1 | 24.7 ± 1.3 | 26.8 ± 1.7 | 24.2 ± 1.2 | 23.4 ± 0.9 |
| EF, % | 58.9 ± 1.3 | 58.1 ± 2.0 | 57.0 ± 2.2 | 60.0 ± 2.9 | 56.1 ± 2.1 | 54.8 ± 1.5 |
| CO, ml/min | 9.59 ± 0.4 | 9.3 ± 0.3 | 11.0 ± 0.6 | 10.5 ± 0.3 | 10.5 ± 0.3 | 8.0 ± 0.6 |
| LVMI | 3.8 ± 0.1 | 4.6 ± 0.1** | 3.7 ± 0.1 | 4.0 ± 0.1$^{\$\$}$ | 4.0 ± 0.1 | 4.2 ± 0.1$^\$$ |

Figure 5A:
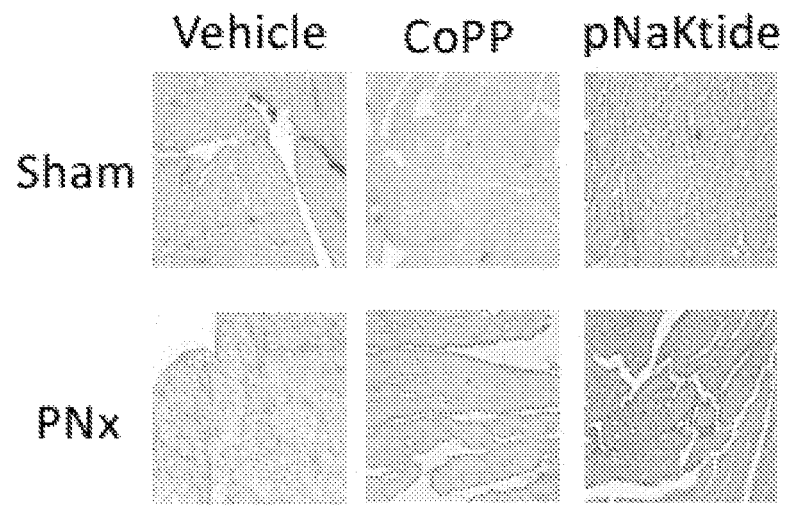
FIGS. 5A-5E include images and graphs showing the effect of pNaKtide and CoPP on PNx-induced cardiac fibrosis.
Figure 5A:
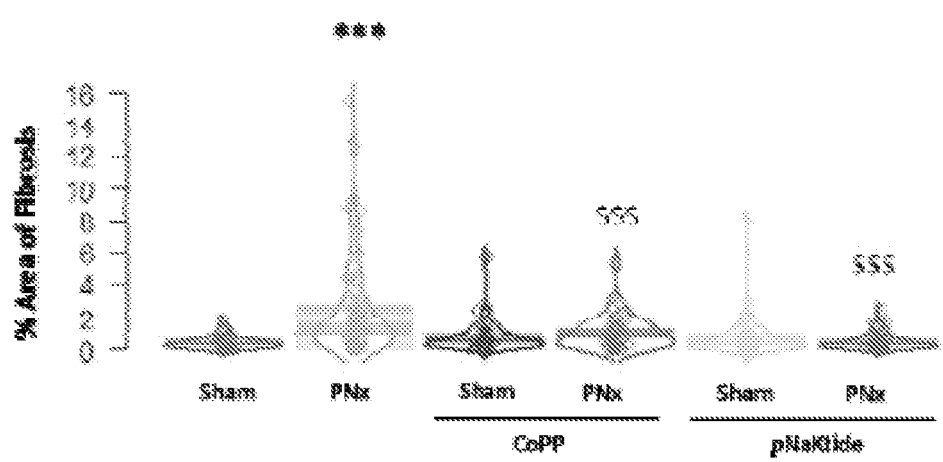

Values are means ± SE, BW, body weight; HR, heart rate; EDA, end diastolic area; ESA, end systolic area; EDD, end diastolic dimension; ESD, end systolic dimension; PWT, posterior wall thickness; AWT, anterior wall thickness; ET, ejection time; IVCT, isovolumic contraction time; IVRT, isovolumic relaxation time; PaVTI, pulmonary artery Velocity time integral; PaD, pulmonary artery dimension; RWT, relative wall thickness; MPI, myocardial performance index; FS, fractional shortening; EF, ejection fraction; CO, cardiac output; LVMI, left ventricle mass index.
*$P < 0.05$,
**$P < 0.01$ PNx vs. Sham;
$^\$P < 0.05$,
$^{\$\$}P < 0.01$ PNx + CoPP or pNaKtide vs. PNx Example 3—Effect of pNaKtide and CoPP on PNx-Induced Cardiac Fibrosis Administration of either pNaKtide or CoPP to sham surgery treated animals did not significantly affect the degree of cardiac fibrosis. PNx surgery was accompanied by marked degrees of cardiac fibrosis as assessed by Sirius Red/Fast Green staining ($p<0.01$ vs Sham) which was significantly attenuated by pNaKtide or CoPP treatment (FIG. 5A, both $p<0.01$ vs. PNx).

Figure 5B:
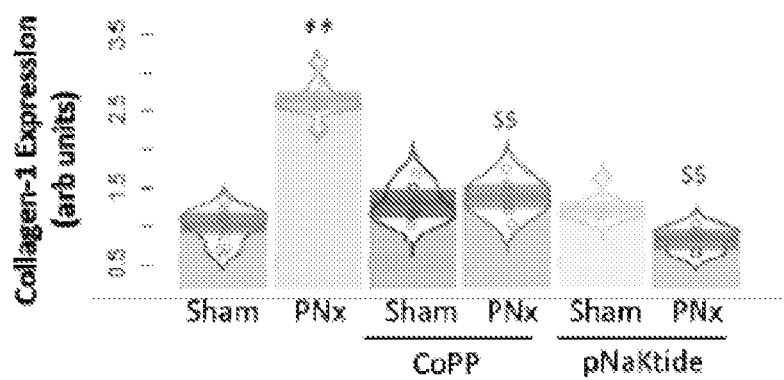
Figure 5C:
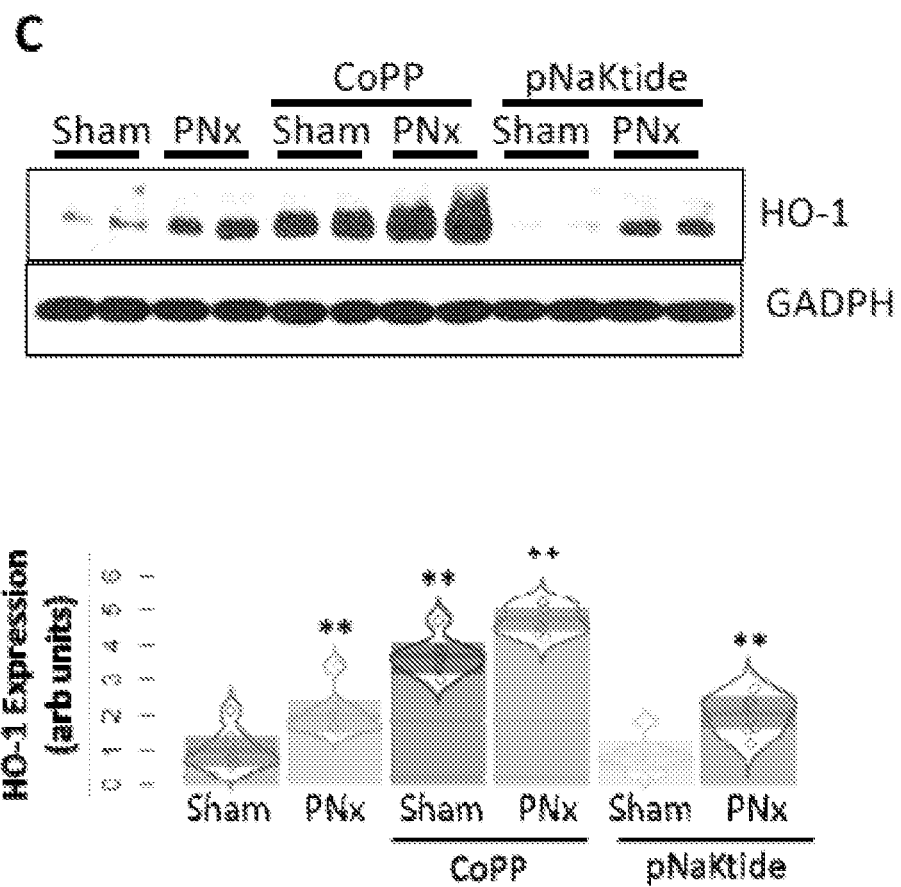

In addition to the morphological changes, PNx significantly increased collagen-1 expression in left ventricle (LV) homogenates assayed by Western blot analysis (FIG. 5B, $p<0.01$ vs Sham). Administration of either pNaKtide or CoPP reduced PNx-induced increases in cardiac collagen-1 expression (FIG. 5B, both $p<0.01$ vs PNx). While CoPP induced HO-1 expression most profoundly, PNx alone also induced HO-1 expression in the LV homogenates (FIG. 5C, $p<0.01$ vs PNx).

Figure 5D:
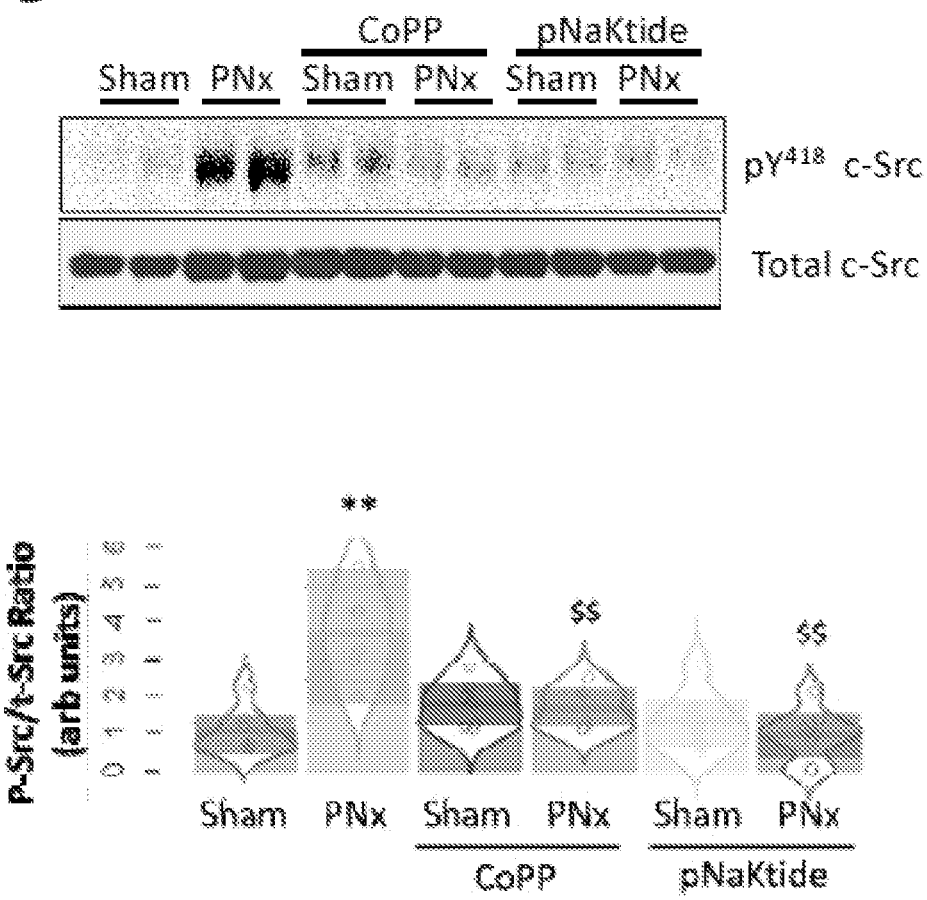
Figure 5E:
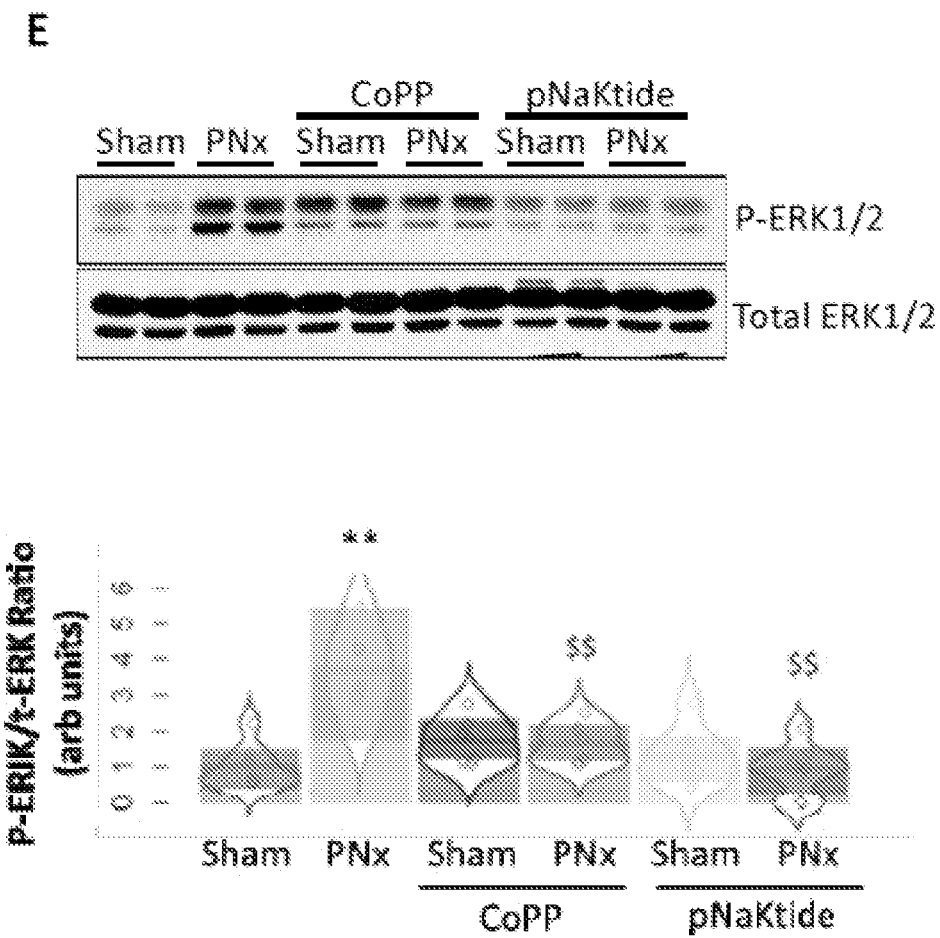
Figure 6A:
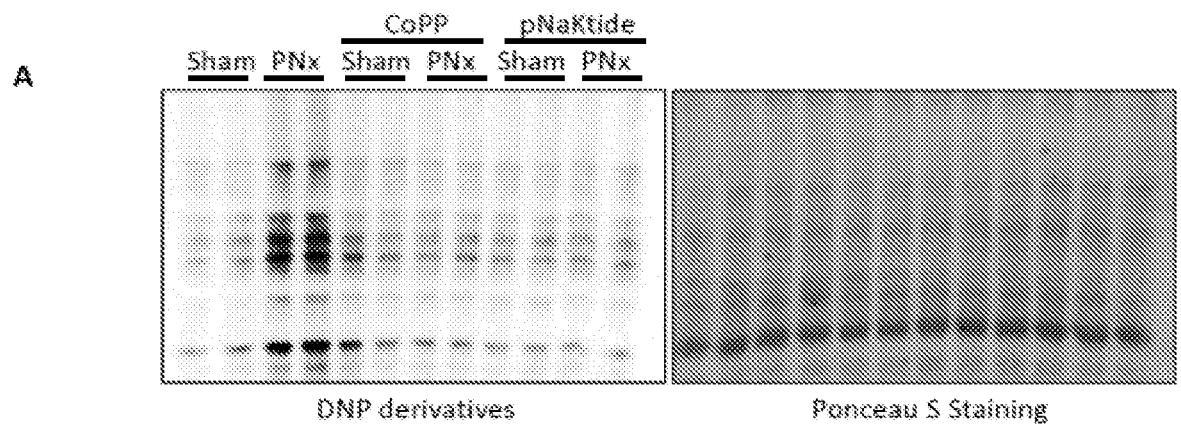
FIGS. 6A-6B include images and graphs showing the effect of pNaKtide and CoPP on the development of cardiac protein carbonylation and c-Src activation following PNx. Representative western blot analysis of protein carbonylation in left ventricle samples with quantitative data (n=6-8 mice per group). **, p<0.01 vs. Sham alone; $$ p<0.01 vs. PNx alone.
Figure 6B:
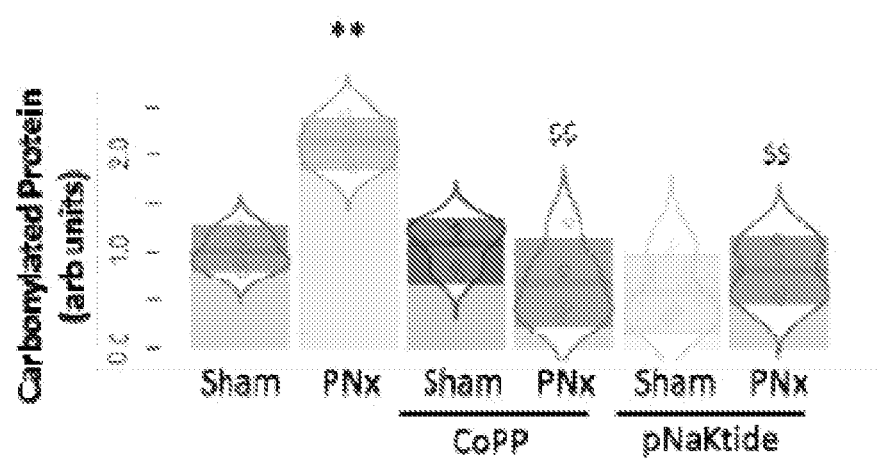
Figure 7:
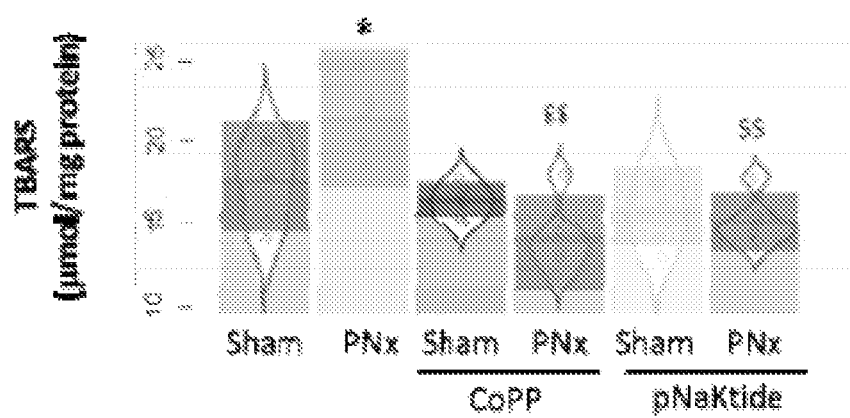
FIG. 7 is a graph showing levels of thiobarbituric acid reactive substances (TBARS) in CoPP and pNaKtide treated PNx mice.

Example 4: Effect of pNaKtide and CoPP on Cardiac Signaling and Oxidant Stress In Vivo At 4 weeks after PNx surgery, a significant activation of c-Src (FIG. 5D, $p<0.01$ vs Sham) and ERK1/2 (FIG. 5E, $p<0.01$ vs Sham) was observed in LV homogenates in PNx group that was attenuated in those PNx animals given CoPP or pNaKtide (both $p<0.01$ vs PNx). Comparing to sham group, PNx stimulated protein carbonylation, an oxidative stress marker, in LV homogenates (FIGS. 6A-6B, $p<0.01$ vs Sham). Administration of CoPP and pNaKtide reduced PNx-induced protein carbonylation (FIGS. 6A-6B, both p<0.01 vs PNx). TBARS data were consistent with the carbonylation data as expected (FIG. 7).

Figure 8A:
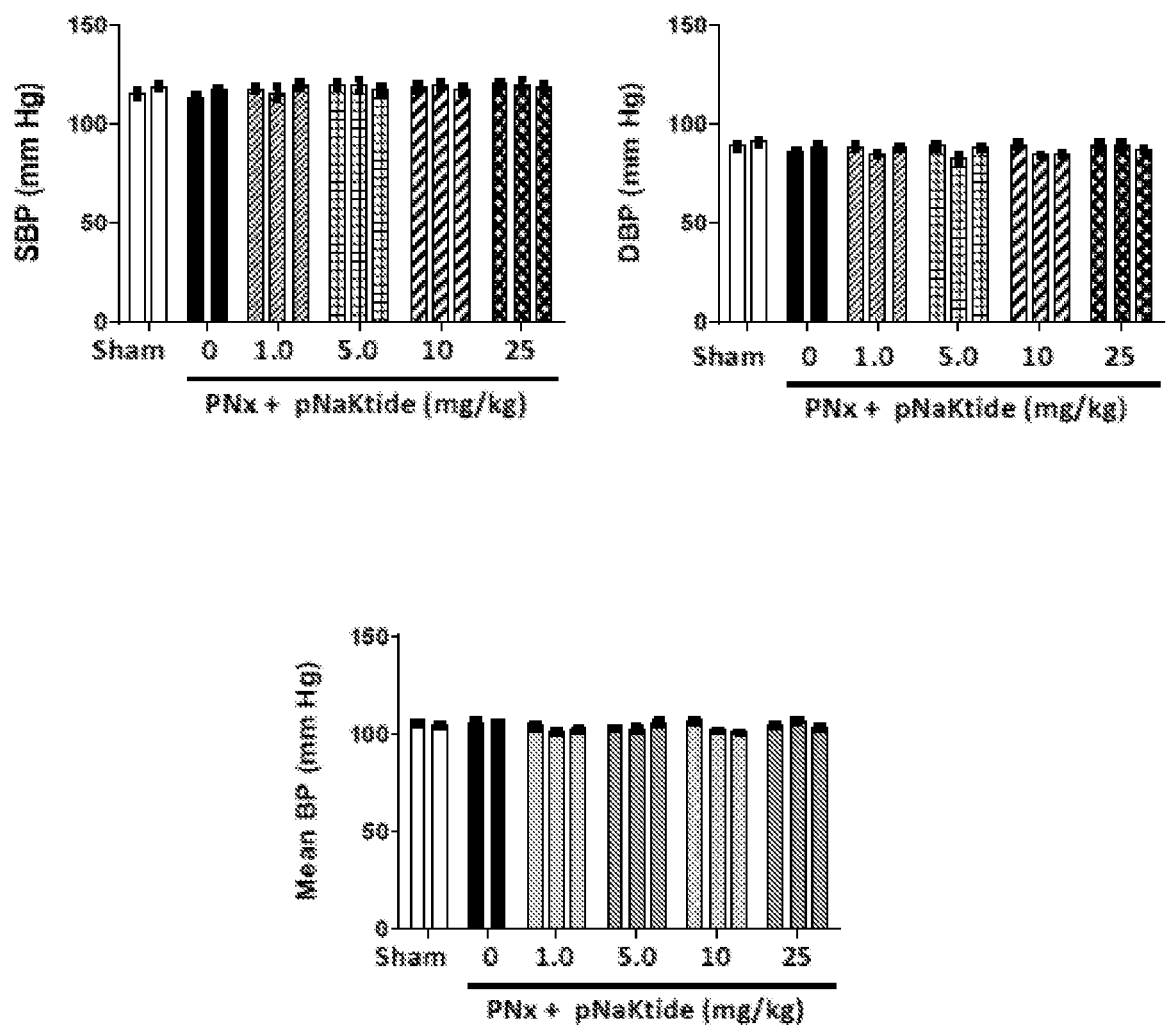
FIGS. 8A-8F include graphs showing that administration of pNaKtide reverses PNx induced uremic cardiomyopathy, including graphs showing the effect of different doses of pNaKtide on blood pressure (FIG. 8A), hematocrit (FIG. 8B), heart weight/body weight ratio, (FIG. 8C), plasma cystatin C (FIG. 8D), creatinine (FIG. 8E), and BUN (FIG. 8F).
Figure 8B:
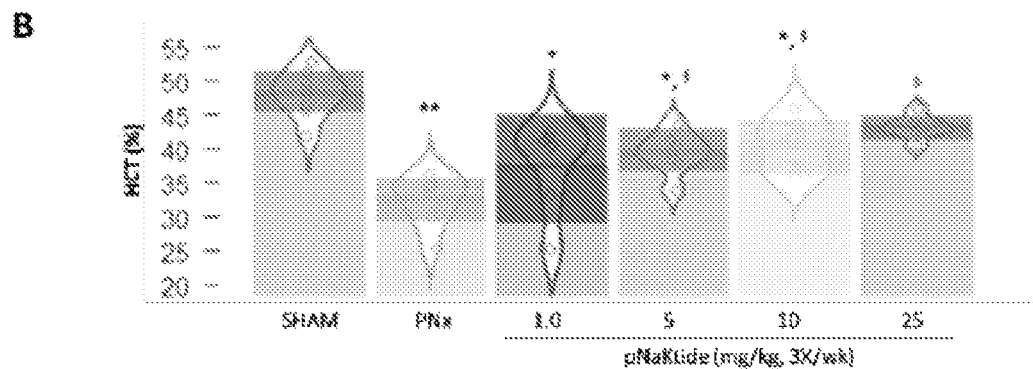
Figure 8C:
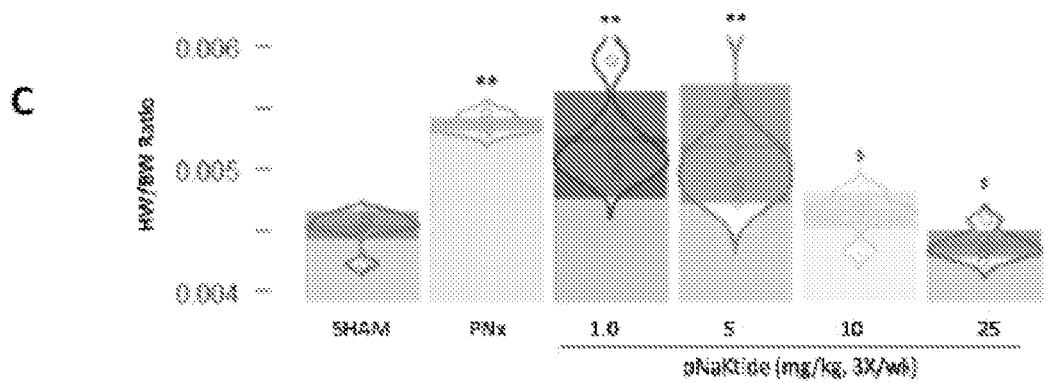
Figure 8D:
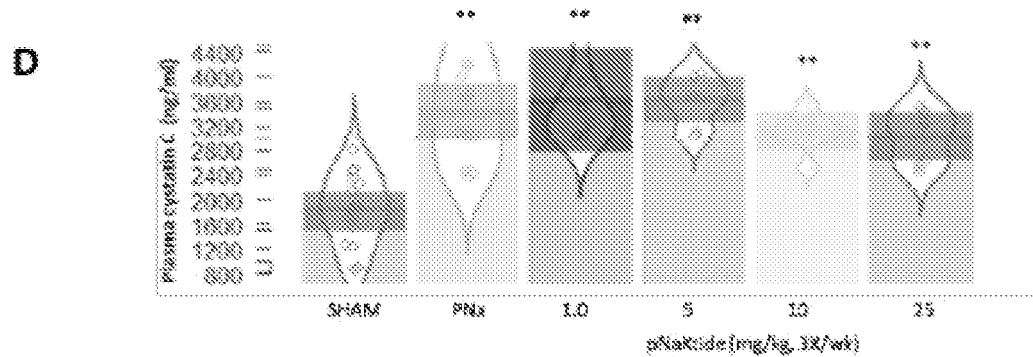
Figure 8E:
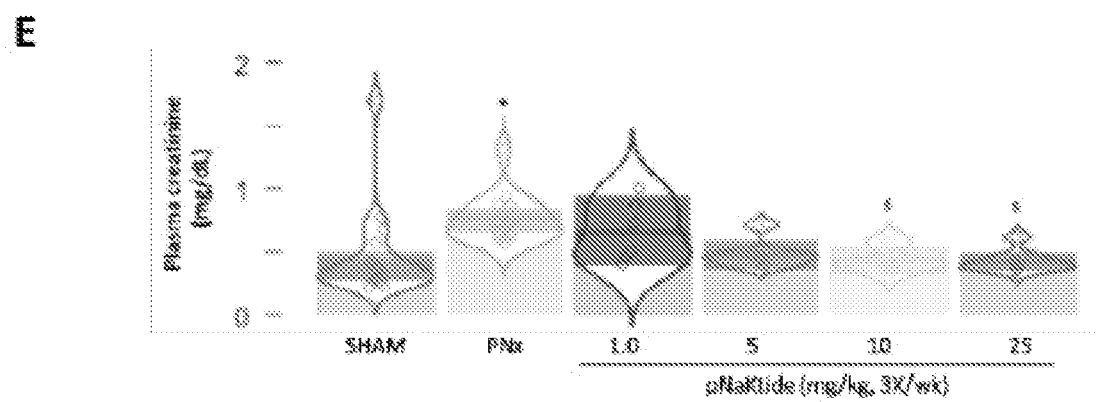
Figure 8F:
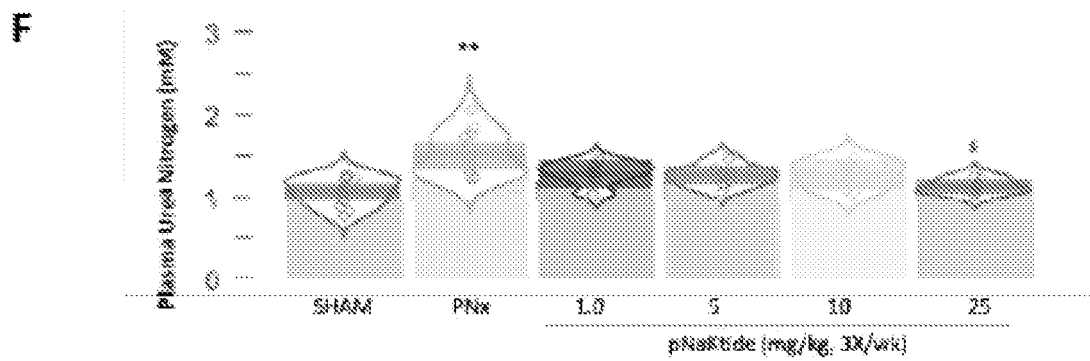

Example 5—Administration of pNaKtide Reverses PNx Induced Uremic Cardiomyopathy—Reversal Study In another set of animals, PNx was performed and mice were allowed to develop uremic cardiomyopathy for 4 weeks. pNaKtide was administered at a dose of either 0, 1, 5, 10 and 25 mg/kg for one week at day 0, day 2, and day 4, and the mice were sacrificed on day 7. Blood pressure measurements and echocardiography were performed both before pNaKtide treatment and sacrifice. In these animals, it was observed that many, but not all, of the echocardiographic features of uremic cardiomyopathy were reversed by pNaKtide in a dose dependent fashion after one week (Table 2). Specifically, wall thickness (anterior, posterior and relative wall thickness) as well as left ventricular mass (LVMI) were ameliorated by pNaKtide at the higher doses. MPI changes which were also ameliorated by pNaKtide in the earlier study was not reversed by pNaKtide in this reversal study. These data are summarized in Table 2. Blood pressure was not affected by the different doses of pNaKtide (FIG. 8A), but the hematocrit increased with pNaKtide treatments in a dose-dependent manner (FIG. 8B). Also, the heart weight/body weight ratio increases induced by PNx was reversed by pNaKtide therapy in a dose dependent fashion (FIG. 8C).

weight/body weight ratio with PNx was also markedly attenuated by administration of higher doses of pNaKtide (FIG. 8C). Administration of higher doses of pNaKtide reversed PNx-mediated increases in plasma creatinine and BUN, but not plasma cystatin C (FIGS. 8D-8E).

Discussion of Example 1-5

Systemic oxidant stress is part of the uremic syndrome, and some believe it plays a critical role in the pathogenesis of the cardiac abnormalities of uremic cardiomyopathy. Oxidant stress in experimental uremic cardiomyopathy has been previously demonstrated, a phenomenon that has been attributed to elevated levels of cardiotonic steroids (CTS) which serve as ligands and activators for the Na/K-ATPase. To this point, antagonism of these CTS through active or passive immunization and through pharmacological strategies is effective at ameliorating physiological, morphological and biochemical features of uremic cardiomyopathy in rodents. On this background, examination of the blockade of the Na/K-ATPase signal cascade with pNaKtide, an agent which does not affect the pumping function of the Na/K-ATPase, was conducted to determine whether it could also effectively ameliorate the phenotypical features of uremic cardiomyopathy. CoPP induction of HO-1 was used to examine whether this was dependent on the specific blockade of Na/K-ATPase oxidant amplification or whether it was a consequence of attenuating the oxidant stress itself.

Data showed that either pNaKtide or CoPP ameliorated the physiological, morphological and biochemical altera-

TABLE 2

Summary of transthoracic echocardiography.

| Variable | PNX vehicle (n = 7) | PNX + 1 mg/kg (n = 6) | PNX + 5 mg/kg (n = 14) | PNX + 10 mg/kg (n = 14) | PNX + 25 mg/kg (n = 7) |
| --- | --- | --- | --- | --- | --- |
| BW, g | 25.3 ± 1.0 | 26.8 ± 0.8 | 25.0 ± 0.8 | 24.1 ± 0.7 | 24.3 ± 0.6 |
| HR, beat/min | 432 ± 26 | 389 ± 6 | 414 ± 9 | 415 ± 9 | 392 ± 20 |
| EDA, mm$^2$ | 27.4 ± 0.4 | 28.0 ± 0.4 | 27.8 ± 0.6 | 27.9 ± 0.6 | 27.5 ± 0.5 |
| ESA, mm$^2$ | 19.4 ± 0.6 | 20.3 ± 0.3 | 20.5 ± 0.7 | 20.6 ± 0.5 | 20.0 ± 0.4 |
| EDD, mm | 4.4 ± 0.1 | 4.7 ± 0.03 | 4.6 ± 0.1 | 4.6 ± 0.1 | 4.5 ± 0.1 |
| ESD, mm | 3.4 ± 0.1 | 3.6 ± 0.02 | 3.6 ± 0.1 | 3.7 ± 0.1 | 3.6 ± 0.1 |
| PWT, mm | 0.62 ± 0.01 | 0.68 ± 0.02 | 0.59 ± 0.01$ | 0.60 ± 0.01$ | 0.62 ± 0.0 |
| AWT, mm | 0.81 ± 0.03 | 0.78 ± 0.01 | 0.68 ± 0.01$$ | 0.64 ± 0.01$$ | 0.63 ± 0.02$$ |
| ET, msec | 45 ± 1.7 | 48 ± 1.2 | 47 ± 1.0 | 50 ± 1.1 | 49 ± 2.1 |
| IVCT + IVRT, msec | 23 ± 0.7 | 27 ± 0.7 | 24 ± 0.8 | 26 ± 0.7 | 24 ± 1.6 |
| PaVTI | 27.1 ± 0.5 | 26.6 ± 0.9 | 26.6 ± 0.8 | 27.2 ± 0.4 | 28.2 ± 0.4 |
| PaD, mm | 1.1 ± 0.02 | 1.0 ± 0.02 | 1.1 ± 0.01 | 1.0 ± 0.01 | 1.0 ± 0.02 |
| RWT | 0.33 ± 0.01 | 0.31 ± 0.01 | 0.27 ± 0.01$$ | 0.27 ± 0.01$$ | 0.28 ± 0.01$$ |
| MPI | 0.51 ± 0.01 | 0.55 ± 0.01 | 0.50 ± 0.01 | 0.52 ± 0.01 | 0.49 ± 0.02 |
| FS, % | 21.0 ± 1.0 | 22.7 ± 0.6 | 21.4 ± 0.8 | 21.1 ± 0.6 | 20.9 ± 1.3 |
| EF, % | 50.9 ± 2.1 | 53.8 ± 1.1 | 51.2 ± 1.5 | 50.7 ± 1.1 | 50.2 ± 2.4 |
| CO, ml/min | 10.5 ± 1.0 | 8.3 ± 0.2 | 9.7 ± 0.5 | 9.0 ± 0.3 | 8.8 ± 0.3 |
| LVMI | 4.7 ± 0.1 | 5.1 ± 0.1 | 4.5 ± 0.1 | 4.4 ± 0.1$ | 4.3 ± 0.1$$ |

Figure 9A:
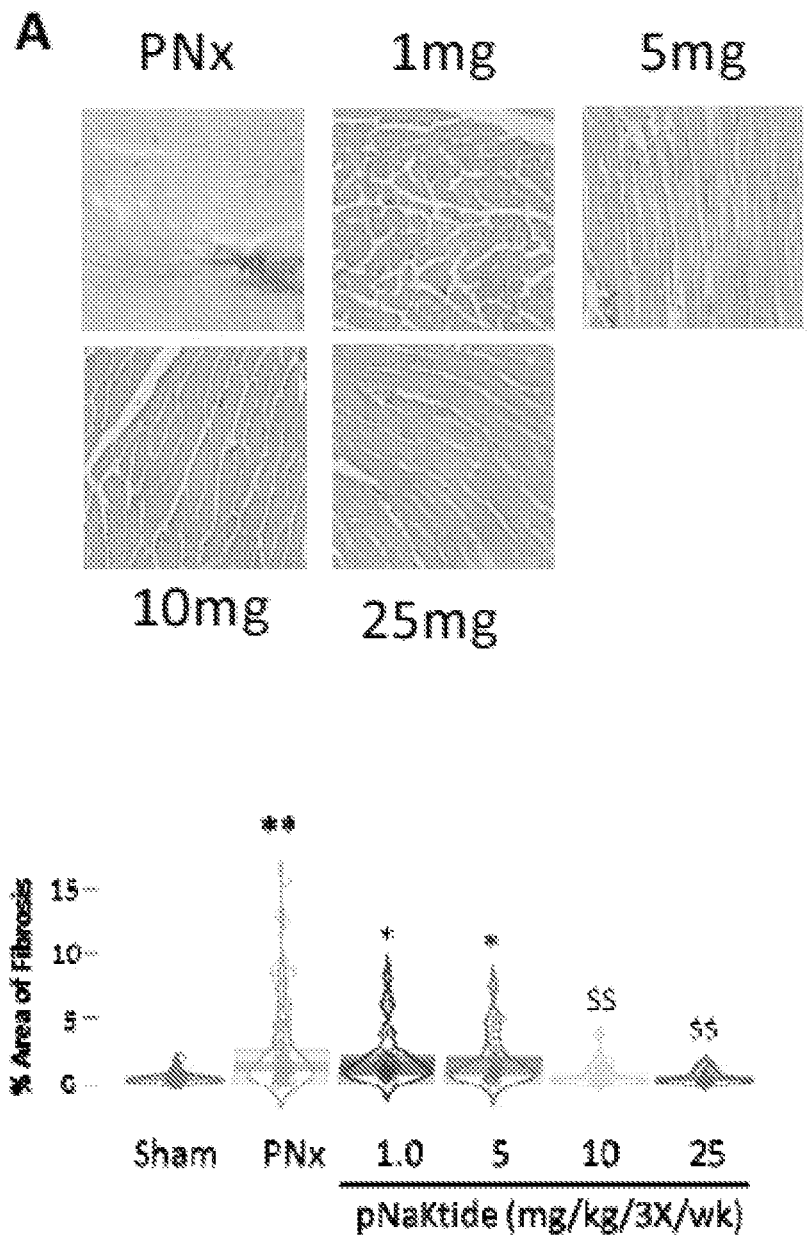
FIGS. 9A-9E include images and graphs showing the effect of pNaKtide on reversal of cardiac fibrosis following PNx as assessed by histology (FIG. 9A), collagen 1-expression (FIG. 9B), cardiac c-Src activation (FIG. 9C), ERK1/2 activation (FIG. 9D), and protein carbonylation (FIG. 9E).
Figure 9B:
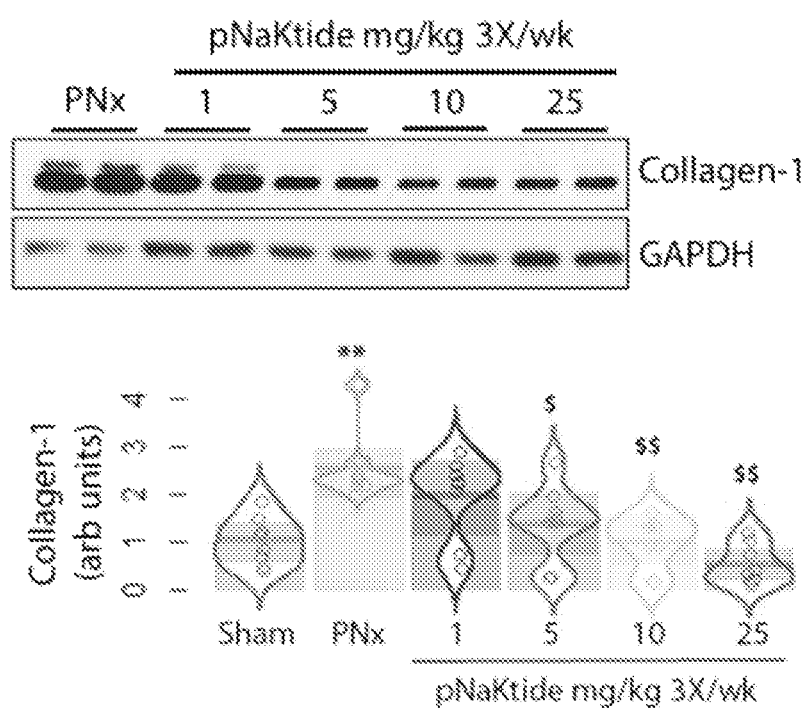
Figure 9C:
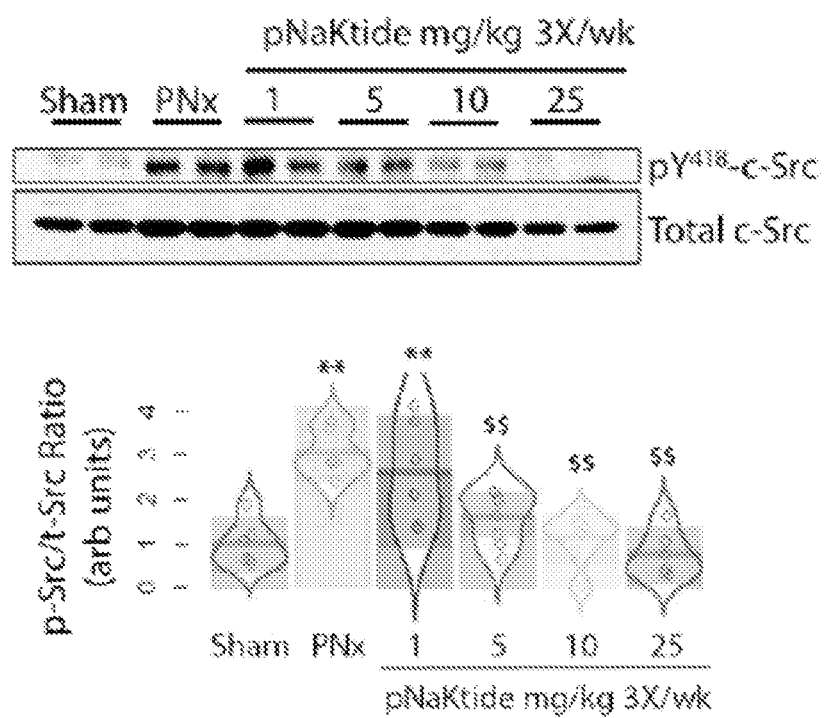
Figure 9D:
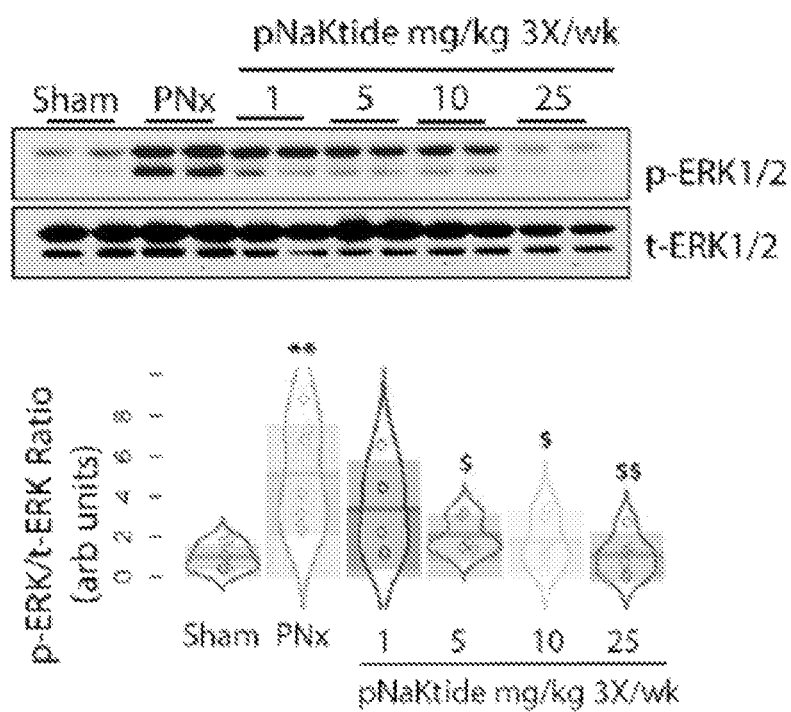
Figure 9E:
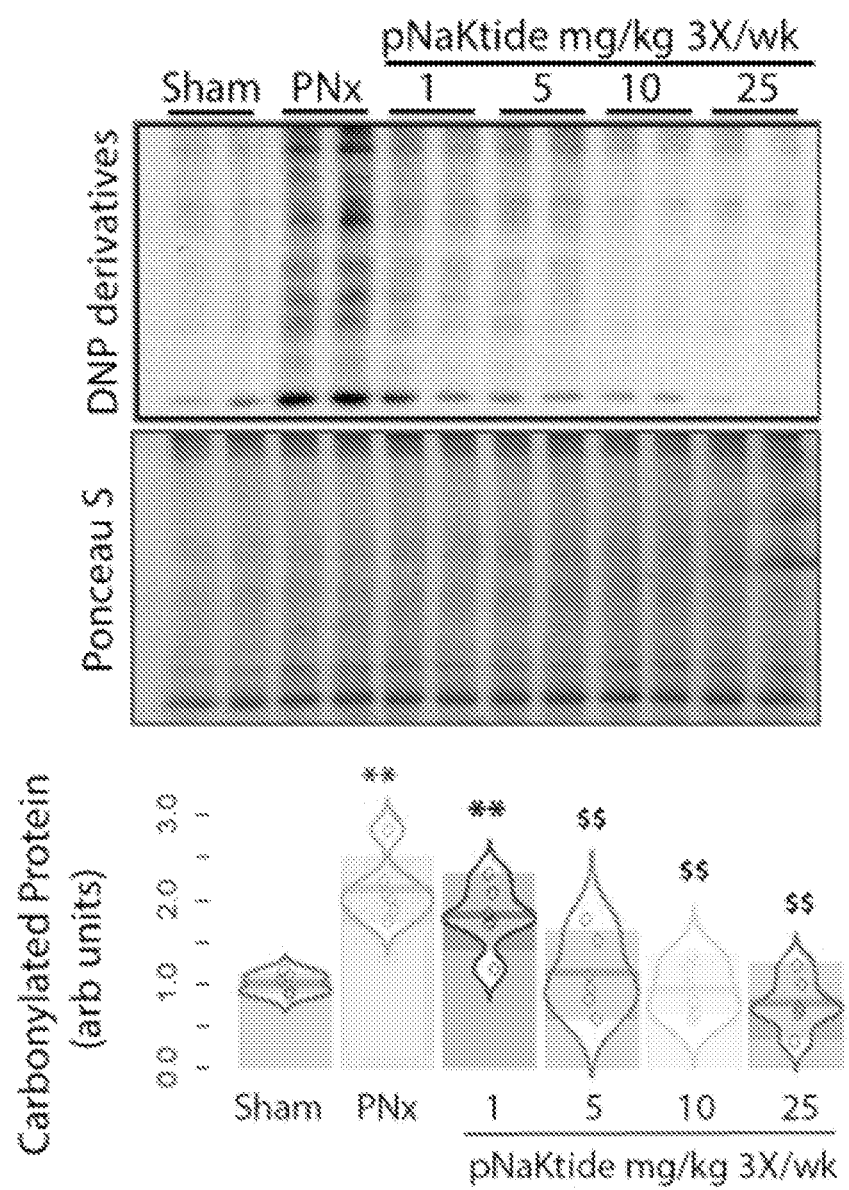

Values are means ± SE, BW, body weight; HR, heart rate; EDA, end diastolic area; ESA, end systolic area; EDD, end diastolic dimension; ESD, end systolic dimension; PWT, posterior wall thickness; AWT, anterior wall thickness; ET, ejection time; IVCT, isovolumic contraction time; IVRT, isovolumic relaxation time; PaVTI, pulmonary artery Velocity time integral; PaD, pulmonary artery dimension; RWT, relative wall thickness; MPI, myocardial performance index; FS, fractional shortening; EF, ejection fraction; CO, cardiac output; LVMI, left ventricle mass index.
$P < 0.05
$$P < 0.01 vs PNx-vehicle In addition to the echocardiographic changes, pNaKtide, at higher doses, also reversed the fibrosis in a dose dependent manner as assessed by histology (FIG. 9A) and collagen 1-expression (FIG. 9B). Treatment with pNaKtide also attenuated cardiac c-Src activation (FIG. 9C) and ERK1/2 activation (FIG. 9D), as well as oxidant stress as assessed by protein carbonylation (FIG. 9E). PNx induced profound anemia was substantially alleviated by administration of higher doses of pNaKtide (FIG. 8B). The increase in heart tions of uremic cardiomyopathy. Specifically, the improvement of oxidant stress with either of these agents resulted in improved left ventricular diastolic function and decreased hypertrophy, less cardiac fibrosis and less evidence for Na/K-ATPase signaling and ROS stress. Surprisingly, amelioration of the anemia associated with chronic renal failure was noted with pNaKtide, but not CoPP. Without being bound by theory, this may be related to different effect durations these agents might have in different tissues. In the murine cardiac fibroblast system, decreasing oxidant stress with either pNaKtide or CoPP attenuated Na/K-ATPase signaling and collagen production to comparable degrees.

The effects of pNaKtide on established cardiac changes in this model were further examined. pNaKtide reversed cardiac hypertrophy and fibrosis in a dose-dependent manner. Interestingly, changes in MPI with PNx, an index of systolic and diastolic function which were prevented by weekly administration of pNaKtide were not affected by the week of pNaKtide therapy in animals with established uremic cardiomyopathy at any dose studied. This either indicates that the functional change(s) measured with MPI are recalcitrant to reversal or pNaKtide was administered for inadequate time. Again surprisingly, one week of pNaKtide administration significantly improved established anemia in our model of experimental renal failure.

The data are of interest for several reasons. First, it suggests a somewhat different interpretation of the "chicken or the egg" argument regarding oxidant stress and inflammation. While some studies have suggested that the oxidant stress in chronic kidney disease results from inflammation presumably due to various uremic toxins, the data suggest that signaling through the Na/K-ATPase may produce the initial oxidant stress which initiates recruitment of inflammation. Second, the data suggest that therapy that allows for the attenuation of oxidant stress can ameliorate phenotypical features of uremic cardiomyopathy. As cardiac mortality is markedly elevated in patients afflicted with advanced renal disease, this suggests effective therapy. Neither HO-1 induction nor pNaKtide represents oxygen radical scavengers. Both strategies involve dynamic attenuation of oxidant stress by decreased production and/or increased detoxification.

SEQUENCE LISTING

SATWLALSRIAGLCNRAVFQ — SEQ ID NO: 1

GRKKRRQRRRPPQ — SEQ ID NO: 2

RQIKIWFQNRRMKWKK — SEQ ID NO: 3

KKGKKGKK — SEQ ID NO: 4

GRKKRRQRRRPPQSATWLALSRIAGLCNRAVFQ — SEQ ID NO: 5

Throughout this document, various references are mentioned. All such references are incorporated herein by reference, including the references set forth in the following list:

REFERENCES

1. J. Liu et al., Ouabain interaction with cardiac Na+/K+-ATPase initiates signal cascades independent of changes in intracellular Na+ and Ca2+ concentrations. *J Biol Chem* 275, 27838-27844 (2000).
2. Z. Xie et al., Intracellular reactive oxygen species mediate the linkage of Na+/K+-ATPase to hypertrophy and its marker genes in cardiac myocytes. *J Biol Chem* 274, 19323-19328 (1999).
3. M. Liang et al., Identification of a pool of non-pumping Na/K-ATPase. *J Biol Chem* 282, 10585-10593 (2007).
4. K. Sodhi et al., pNaKtide inhibits Na/K-ATPase reactive oxygen species amplification and attenuates adipogenesis. *Sci Adv* 1, e1500781 (2015).
5. Y. Yan et al., Involvement of reactive oxygen species in a feed-forward mechanism of Na/K-ATPase-mediated signaling transduction. *J Biol Chem* 288, 34249-34258 (2013).
6. Z. Li et al., Na/K-ATPase mimetic pNaKtide peptide inhibits the growth of human cancer cells. *J Biol Chem* 286, 32394-32403 (2011).
7. Z. Li et al., NaKtide, a Na/K-ATPase-derived peptide Src inhibitor, antagonizes ouabain-activated signal transduction in cultured cells. *J Biol Chem* 284, 21066-21076 (2009).
8. J. Lee, S. Kim, Upregulation of heme oxygenase-1 expression by dehydrodiconiferyl alcohol (DHCA) through the AMPK-Nrf2 dependent pathway. *Toxicol Appl Pharmacol* 281, 87-100 (2014).
9. Y. Issan et al., Heme oxygenase-1 induction improves cardiac function following myocardial ischemia by reducing oxidative stress. *PLoS One* 9, e92246 (2014).
10. A. Asija, S. J. Peterson, D. E. Stec, N. G. Abraham, Targeting endothelial cells with heme oxygenase-1 gene using VE-cadherin promoter attenuates hyperglycemia-mediated cell injury and apoptosis. *Antioxid Redox Signal* 9, 2065-2074 (2007).
11. F. T. Botros et al., Induction of heme oxygenase-1 in renovascular hypertension is associated with inhibition of apoptosis. *Cell Mot Biol (Noisy-le-grand)* 53, 51-60 (2007).
12. G. M. London, P. S. Parfrey, Cardiac disease in chronic uremia: pathogenesis. *Adv Ren Replace Ther* 4, 194-211 (1997).
13. B. Mohmand, D. K. Malhotra, J. I. Shapiro, Uremic cardiomyopathy: role of circulating *digitalis* like substances. *Front Biosci* 10, 2036-2044 (2005).
14. J. Himmelfarb, E. McMonagle, Manifestations of oxidant stress in uremia. *Blood Purif* 19, 200-205 (2001).
15. D. M. Okamura, J. Himmelfarb, Tipping the redox balance of oxidative stress in fibrogenic pathways in chronic kidney disease. *Pediatr Nephrol* 24, 2309-2319 (2009).
16. J. Himmelfarb, P. Stenvinkel, T. A. Ikizler, R. M. Hakim, The elephant in uremia: oxidant stress as a unifying concept of cardiovascular disease in uremia. *Kidney Int* 62, 1524-1538 (2002).
17. B. N. Becker, J. Himmelfarb, W. L. Henrich, R. M. Hakim, Reassessing the cardiac risk profile in chronic hemodialysis patients: a hypothesis on the role of oxidant stress and other non-traditional cardiac risk factors. *J Am Soc Nephrol* 8, 475-486 (1997).
18. D. J. Kennedy et al., Partial nephrectomy as a model for uremic cardiomyopathy in the mouse. *Am J Physiol Renal Physiol* 294, F450-454 (2008).
19. D. J. Kennedy et al., Central role for the cardiotonic steroid marinobufagenin in the pathogenesis of experimental uremic cardiomyopathy. *Hypertension* 47, 488-495 (2006).
20. C. A. Drummond et al., Reduction of Na/K-ATPase affects cardiac remodeling and increases c-kit cell abundance in partial nephrectomized mice. *Am J Physiol Heart Circ Physiol* 306, H1631-1643 (2014).
21. S. T. Haller et al., Monoclonal antibody against marinobufagenin reverses cardiac fibrosis in rats with chronic renal failure. *Am J Hypertens* 25, 690-696 (2012).

22. J. Tian et al., Spironolactone attenuates experimental uremic cardiomyopathy by antagonizing marinobufagenin. *Hypertension* 54, 1313-1320 (2009).
23. R. N. Foley et al., Mode of dialysis therapy and mortality in end-stage renal disease. *J Am Soc Nephrol* 9, 267-276 (1998).
24. RStudio-Team, RStudio: Integrated Development for R. RStudio, Inc. Boston, MA. 2015.
25. R-Core-Team, R: A language and environment for statistical computing. R Foundation for Statistical Computing. Vienna, Austria. 2016.
26. N. Phillips, yarn: A companion to the e-book YaRrr!: The Pirate's Guide to R. R package version 0.1. 2016.
27. J. K. Kruschke, Bayesian estimation supersedes the t test. *J Exp Psychol Gen* 142, 573-603 (2013).

It will be understood that various details of the presently disclosed subject matter can be changed without departing from the scope of the subject matter disclosed herein. Furthermore, the description provided herein is for the purpose of illustration only, and not for the purpose of limitation.

What is claimed is:

1. A method for treating anemia, comprising administering a polypeptide antagonist of a Na/K ATPase/Src receptor complex to a subject in need thereof, wherein the polypeptide anatagonist comprises the sequence of SEQ ID NO: 1 or a functional fragment thereof, and wherein the anemia is chronic kidney disease-induced anemia.

2. The method of claim 1, wherein administering the polypeptide antagonist comprises administering an amount of the polypeptide antagonist sufficient to increase an amount of hematocrit in the subject.

3. The method of claim 1, wherein the anemia is profound anemia.

4. The method of claim 1, wherein the polypeptide anatagonist further includes a cell penetrating polypeptide encoded by an amino acid sequence selected from the group consisting of SEQ ID NOS: 2-4.

5. The method of claim 1, wherein the administering step includes oral administration, transdermal administration, administration by inhalation, nasal administration, topical administration, intraaural administration, rectal administration, intravenous administration, intramuscular administration, subcutaneous administration, intravitreous administration, subconjunctival administration, intracameral administration, intraocular administration or combinations thereof.

* * * * *

SEQUENCE LISTING

```
<160> NUMBER OF SEQ ID NOS: 5

<210> SEQ ID NO 1
<211> LENGTH: 20
<212> TYPE: PRT
<213> ORGANISM: Homo sapiens

<400> SEQUENCE: 1

Ser Ala Thr Trp Leu Ala Leu Ser Arg Ile Ala Gly Leu Cys Asn Arg
1               5                   10                  15

Ala Val Phe Gln
            20

<210> SEQ ID NO 2
<211> LENGTH: 13
<212> TYPE: PRT
<213> ORGANISM: Human immunodeficiency virus

<400> SEQUENCE: 2

Gly Arg Lys Lys Arg Arg Gln Arg Arg Arg Pro Pro Gln
1               5                   10

<210> SEQ ID NO 3
<211> LENGTH: 16
<212> TYPE: PRT
<213> ORGANISM: Drosophila melanogaster

<400> SEQUENCE: 3

Arg Gln Ile Lys Ile Trp Phe Gln Asn Arg Arg Met Lys Trp Lys Lys
1               5                   10                  15

<210> SEQ ID NO 4
<211> LENGTH: 8
<212> TYPE: PRT
<213> ORGANISM: Homo sapiens

<400> SEQUENCE: 4

Lys Lys Gly Lys Lys Gly Lys Lys
1               5

<210> SEQ ID NO 5
<211> LENGTH: 33
<212> TYPE: PRT
<213> ORGANISM: Artificial Sequence
```

-continued

```
<220> FEATURE:
<223> OTHER INFORMATION: TAT NaKtide Fusion Polypeptide

<400> SEQUENCE: 5

Gly Arg Lys Lys Arg Arg Gln Arg Arg Pro Pro Gln Ser Ala Thr
1               5                   10                  15

Trp Leu Ala Leu Ser Arg Ile Ala Gly Leu Cys Asn Arg Ala Val Phe
            20                  25                  30

Gln
```